(12) United States Patent
Puleo et al.

(10) Patent No.: US 11,318,330 B2
(45) Date of Patent: May 3, 2022

(54) NEUROMODULATION TECHNIQUES

(71) Applicant: General Electric Company, Schenectady, NY (US)

(72) Inventors: Christopher Michael Puleo, Niskayuna, NY (US); Lakshmi Sireesha Kaanumalle, Schenectady, NY (US); Victoria Eugenia Cotero, Troy, NY (US); John Frederick Graf, Ballston Lake, NY (US)

(73) Assignee: GENERAL ELECTRIC COMPANY, Niskayuna, NY (US)

( * ) Notice: Subject to any disclaimer, the term of this patent is extended or adjusted under 35 U.S.C. 154(b) by 367 days.

(21) Appl. No.: 16/143,255

(22) Filed: Sep. 26, 2018

(65) Prior Publication Data

US 2020/0094079 A1 Mar. 26, 2020

(51) Int. Cl.
*A61N 7/00* (2006.01)
*A61N 1/36* (2006.01)
*G01N 33/68* (2006.01)

(52) U.S. Cl.
CPC .......... *A61N 7/00* (2013.01); *A61N 1/36189* (2013.01); *G01N 33/68* (2013.01); *A61N 2007/0004* (2013.01)

(58) Field of Classification Search
CPC .................. A61N 1/36189; A61N 7/00; A61N 2007/0004; A61N 2007/0026; A61N 2007/0021; G01N 33/68
See application file for complete search history.

(56) References Cited

U.S. PATENT DOCUMENTS

| 9,510,777 | B2 | 12/2016 | Hezi-Yamit et al. | |
|---|---|---|---|---|
| 9,877,892 | B2 | 1/2018 | Grant et al. | |
| 2005/0240126 | A1* | 10/2005 | Foley | A61B 8/4209 601/2 |
| 2011/0178441 | A1* | 7/2011 | Tyler | A61B 5/0476 601/2 |
| 2013/0282001 | A1* | 10/2013 | Hezi-Yamit | A61B 5/201 606/33 |
| 2014/0243714 | A1 | 8/2014 | Ward et al. | |

(Continued)

FOREIGN PATENT DOCUMENTS

| WO | 2017035767 A1 | 3/2017 |
|---|---|---|
| WO | 2018081826 A1 | 5/2018 |

OTHER PUBLICATIONS

Harle, J., et al.; "Effects of Therapeutic Ultrasound on Osteoblast Gene Expression", Database accession #E2002046838353, Journal of Materials Science: Materials in medicine 2001 Kluwer Academic Publishers, vol. 12, No. 10-12, 2001, pp. 1-14.

(Continued)

*Primary Examiner* — Rochelle D Turchen
*Assistant Examiner* — Chao Sheng
(74) *Attorney, Agent, or Firm* — Fletcher Yoder, P.C.

(57) ABSTRACT

The subject matter of the present disclosure generally relates to techniques for following a treatment protocol having one or more treatment parameters to cause a targeted physiological outcome at a distal site, assessing an expression level of a gene in a region of interest after completing the treatment protocol, and modifying the one or more treatment parameters based on the expression level of the gene. The treatment protocol may include one or more ultrasound energy treatments to the region of interest.

16 Claims, 26 Drawing Sheets

(56) References Cited

U.S. PATENT DOCUMENTS

| | | | |
|---|---|---|---|
| 2014/0343463 A1* | 11/2014 | Mishelevich | A61N 7/02 |
| | | | 601/2 |
| 2015/0025422 A1* | 1/2015 | Tyler | A61N 5/062 |
| | | | 601/2 |
| 2015/0360026 A1 | 12/2015 | Wagner | |
| 2020/0046992 A1* | 2/2020 | Tracey | A61N 1/40 |

OTHER PUBLICATIONS

Tufail, Yusuf, et al.; "Ultrasonic Neuromodulation by Brain Stimulation with Transcranial Ultrasound", Natural Protocols, vol. 6, No. 9, 2011, pp. 1453-1470.

International Search Report and Written Opinion; PCT/US2019/049128, dated Jan. 20, 2020, 14 pages.

Luedde, Tom, et al.; "C/EBP beta isoforms LIP and LAP modulate progression of the cell cycle in the regenerating mouse liver", Hepatology, vol. 40, Issue: 02, pp. 356-365, Aug. 2004.

Al-Mahrouki, Azza A., et al.; "Bioeffects of ultrasound-stimulated microbubbles on Endothelial cells: gene expression changes associated with Radiation enhancement in vitro", Ultrasound in Medicine & Biology, vol. 38, Issue: 11, pp. 1958-1969, Nov. 2012.

Cain, Derek W., et al.; "Identification of a tissue-specific, C/EBPβ-dependent pathway of differentiation for murine peritoneal macrophages", Journal of Immunology, vol. 191, Issue: 9, pp. 4665-4675, Nov. 2013.

Lim, Mi Hyun, et al.; "Effects of low-intensity ultrasound on gramicidin D-induced erythrocyte edema", Journal of Ultrasound in Medicine, vol. 33, Issue: 06, pp. 949-957, Jun. 2014.

* cited by examiner

NEUROMODULATION TECHNIQUES

BACKGROUND

The subject matter disclosed herein relates to neuromodulation and more specifically, to techniques for modulating a physiological response using energy applied from an energy source.

Neuromodulation has been used to treat a variety of clinical conditions. For example, electrical stimulation at various locations along the spinal cord has been used to treat chronic back pain. An implantable device may periodically generate electrical energy that is applied to a tissue to activate certain nerve fibers, which may result in a decreased sensation of pain. With regard to spinal cord stimulation, the stimulating electrodes are generally positioned in the epidural space, although the pulse generator may be positioned somewhat remotely from the electrodes, e.g., in the abdominal or gluteal region, but connected to the electrodes via conducting wires. In other implementations, deep brain stimulation may be used to stimulate particular areas of the brain to treat movement disorders, and the stimulation locations may be guided by neuroimaging. Such central nervous system stimulation is generally targeted to the local nerve or brain cell function and is mediated by electrodes that deliver electrical pulses and that are positioned at or near the target nerves. However, positioning electrodes at or near the target nerves is challenging. For example, such techniques may involve surgical placement of the electrodes that deliver the energy. In addition, specific tissue targeting via neuromodulation is challenging. Electrodes that are positioned at or near certain target nerves mediate neuromodulation by triggering an action potential in the nerve fibers, which in turn results in neurotransmitter release at a nerve synapse and synaptic communication with the next nerve. Such propagation may result in a relatively larger or more diffuse physiological effect than desired, as current implementation of implanted electrodes stimulate many nerves or axons at once. Because the neural pathways are complex and interconnected, a more targeted modulated effect may be more clinically useful.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible embodiments. Indeed, the disclosure may encompass a variety of forms that may be similar to or different from the embodiments set forth below.

In one embodiment, a method may include following a treatment protocol having one or more treatment parameters to cause a change in concentration of one or more molecules of interest at a distal site. The treatment protocol may include one or more ultrasound energy treatments to a region of interest. The method may include assessing an expression level of a gene in the region of interest and the concentration of the one or more molecules of interest at the distal site after completing the treatment protocol, and modifying the one or more treatment parameters based on the expression level of the gene, the concentration of the one or more molecules of interest, or both.

In another embodiment, a method may include following a treatment protocol having one or more treatment parameters to cause a targeted physiological outcome at a distal site. The treatment protocol may include one or more ultrasound energy treatments to a region of interest. The method may include assessing an expression level of a gene in the region of interest after completing the treatment protocol, and modifying the one or more treatment parameters based on the expression level of the gene.

In another embodiment, a method may include following a treatment protocol having one or more treatment parameters to cause a change in concentration of one or more molecules of interest at a distal site. The treatment protocol may include one or more ultrasound energy treatments to a region of interest. The method may include assessing RNA transcription of a gene in the region of interest, and modifying the one or more treatment parameters based on the RNA transcription of the gene in the region of interest.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
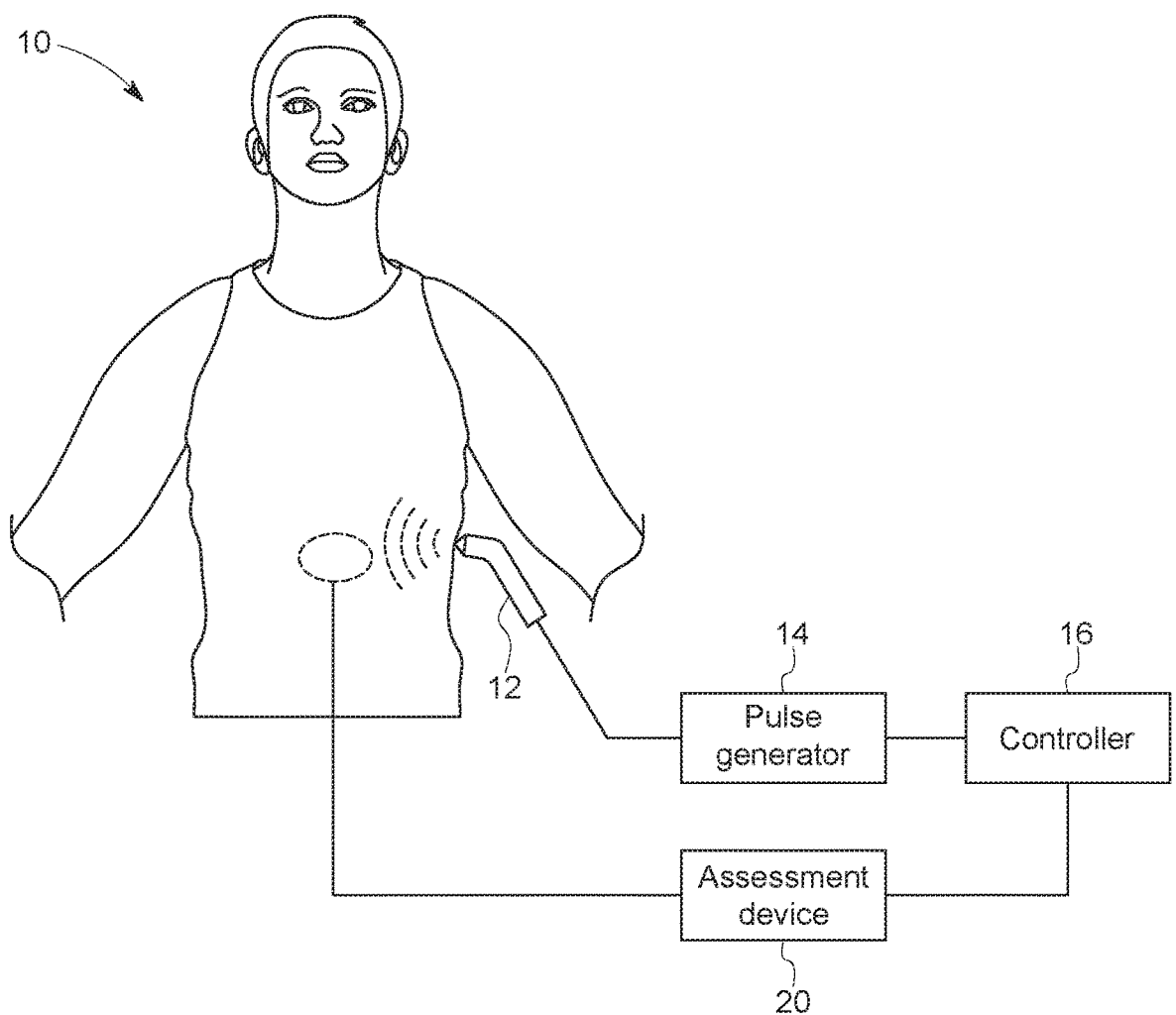
FIG. 1 is a schematic representation of a neuromodulation system using a pulse generator according to embodiments of the disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Any examples or illustrations given herein are not to be regarded in any way as restrictions on, limits to, or express definitions of, any term or terms with which they are utilized. Instead, these examples or illustrations are to be regarded as being described with respect to various particular embodiments and as illustrative only. Those of ordinary skill in the art will appreciate that any term or terms with which these examples or illustrations are utilized will encompass other embodiments that may or may not be given therewith or elsewhere in the specification and all such embodiments are intended to be included within the scope of that term or terms. Language designating such non-limiting examples and illustrations includes, but is not limited to: "for example," "for instance," "such as," "e.g.," "including," "in certain embodiments", "in some embodiments", and "in one (an) embodiment."

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

Provided herein are neuromodulation techniques that are used to treat a subject via the application of energy to areas of the tissue or other anatomical structures at sites where nerves terminate. The energy applied may be targeted to subregions of the tissue or structures, such that the overall energy applied is relatively low. Further, by targeting specific regions of interest, particular neural pathways may be selectively modulated while other, non-targeted, neural pathways outside of the region of interest remain unmodulated. In this manner, neuromodulation of one subregion of an organ may yield a different targeted physiologic outcome than neuromodulation of a different subregion of an organ. In a specific example, targeting a porta hepatis region of a liver with neuromodulating energy may cause a change in a concentration of circulating glucose as a result. Targeting other regions of the liver may not yield the same changes in circulating glucose concentration. In another example, targeting a region of a spleen with neuromodulating energy may cause a change in concentration of norepinephrine and acetylcholine. Further, neuromodulation of peripheral nerve ganglia may modulate the cholinergic anti-inflammatory pathway, dopamine production pathways, and glucose regulatory and/or insulin production pathways. Accordingly, the distribution of nerve endings (e.g., axon terminals) within organs may in turn permit selective neuromodulation to achieve a targeted physiological outcome depending on the nerve or nerves that are directly targeted with neuromodulating energy. Such techniques in peripheral nerves achieve targeted effects propagating at the ends of a peripheral neural pathway. However, the targeted physiological outcome may involve changes in activity in multiple and overlapping pathways.

As discussed herein, neuromodulation may be implemented to cause targeted physiological outcomes, e.g., for the treatment of certain disorders. Patients may benefit from a treatment regimen of neuromodulation at regular intervals (e.g., daily) over a period of time (e.g., weeks) to achieve the desired targeted physiological outcomes. However, the changes in activity in the multiple and overlapping pathways may, over time, result in compensatory physiological effects that render the neuromodulation treatments less effective over time. Accordingly, the present techniques provide an assessment of markers of multiple pathways such that the effectiveness of the neuromodulation may be assessed. In cases of diminishing returns, the treatment regimen may incorporate a recovery period to allow the compensatory pathways to return to normal before restarting neuromodulation. In one embodiment, the assessment is a characteristic profile of gene expression of a plurality of markers, in which certain profiles are associated with physiological changes that diminish the effectiveness of neuromodulation while other profiles are associated with a favorable gene expression environment for effective neuromodulation. The characteristic gene expression or marker expression profiles are indicative of the complex physiological changes that are propagated via the application of energy to nerve axon terminals in the neuromodulation implementations provided herein. In another embodiment, the characteristic profile relates to changes in concentration or modifications of one or more molecules (e.g., circulating molecules, biomarkers) of interest.

The human nervous system is a complex network of nerve cells, or neurons, found centrally in the brain and spinal cord and peripherally in the various nerves of the body. Neurons have a cell body, dendrites, and an axon. A nerve is a group of neurons that serve a particular part of the body. Nerves may contain several hundred neurons to several hundred thousand neurons. Nerves often contain both afferent and efferent neurons. Afferent neurons carry signals to the central nervous system and efferent neurons carry signals to the periphery. A group of neuronal cell bodies in one location is known as a ganglion. Electrical signals generated in the nerves (e.g., via intrinsic or external stimulation) are conducted via neurons and nerves. Neurons release neurotransmitters at synapses (connections) adjacent to a receiving cell to allow continuation and modulation of the electrical signals.

The electrical signal of a neuron is known as an action potential. Action potentials are initiated when a voltage potential across the cell membrane exceeds a certain threshold. This action potential is then propagated down the length of the neuron. The action potential of a nerve is complex and represents the sum of action potentials of the individual neurons in it. The junction between the axon terminals of a neuron and the receiving cell is called a synapse. Action potentials travel down the axon of the neurons to its axon terminal, which is the distal termination of the branches of an axon nerve that forms a presynaptic ending or a synaptic terminal of the nerve fiber. The electrical impulse of the action potential triggers the migration of vesicles containing neurotransmitters to a presynaptic membrane of the presynaptic axon terminal and, ultimately, the release of the neurotransmitters into a synaptic cleft (e.g., the space formed between the presynaptic and the postsynaptic cell) or the axoextracellular space. A chemical synapse converts the electrical signal of an action potential to a chemical signal by releasing neurotransmitters. In contrast to chemical synapses, electrical synapses allow ionic currents to flow into a presynaptic axon terminal and across the cell membranes into a postsynaptic cell.

The physiological effect of the action potential is mediated by ion movement across a cell membrane. Neurons actively maintain a resting membrane potential via ion pumps that facilitate movement of ions such as $Na^+$, $K^+$, $Cl^-$ and through the neuronal membrane. Different types of neurons may maintain different resting membrane potentials (e.g., $-75$ mV to $-55$ mV). An action potential is generated by an influx of ions (i.e., a movement of charge) to generate a large deviation in the membrane potential that is associated with a temporary rise in voltage across the membrane. For example, the rise in the membrane potential may be in a range of 30 mV to 60 mV. An action potential in a postsynaptic neuron may initiate in response to a release of neurotransmitters from a presynaptic (e.g., upstream) neuron. The neurotransmitters released from the presynaptic neuron bind to receptors at the postsynaptic neuron, which in turn causes an influx of ions and subsequent depolarization across the membrane. The action potential is then propagated along the nerve as this process occurs between subsequent neurons within the nerve.

Synapses may be located at a junction between two neurons, which permits an action potential to be propagated down a nerve fiber. However, axon terminals may also form synapses at the junctions between neurons and non-neuronal cells or may terminate at interstitial fluid or body fluid. Types of synapses, for example, include synapses with immune cells at a neuroimmune junction, synapses with resident sensory cells within an organ, or synapses with gland cells. The release of neurotransmitters into a synaptic cleft and the binding of the neurotransmitters to receptors in a postsynaptic membrane of a postsynaptic cell results in downstream effects that are dependent on the nature of the presynaptic neuron, the specific neurotransmitters released, and the nature of the postsynaptic cell (e.g., types of available receptors of the postsynaptic cell). Additionally, an action potential may be excitatory or inhibitory. An excitatory postsynaptic action potential increases the likelihood of the postsynaptic neuron to fire or release a subsequent action potential. In contrast, an inhibitory postsynaptic action potential decreases the likelihood of a postsynaptic neuron to fire or release a subsequent action potential. Several neurons may work together to release neurotransmitters that trigger downstream action potentials or inhibit downstream action potentials.

Neuromodulation applies energy from an external energy source to certain areas of the nervous system to activate and/or block one or more nerves or increase and/or decrease nerve function. Electrical neuromodulation applies one or more electrodes at or near target nerves, and the applied energy is carried through the nerve (e.g., as an action potential) to cause a physiological response in areas of the downstream of the energy application site. However, it is difficult to predict the scope and eventual endpoint of the physiological response for a given energy application site because of the complexity of the nervous system. While strategies for ultrasound modulation of the central nervous system (i.e. brain tissue) have demonstrated successful modulation of neural activity, attempts to modulate peripheral nerves have lagged. For example, ultrasound modulation of the central nervous system (CNS) involves stimulation of cortical regions of the brain, which are rich in synaptic structures while attempts at ultrasound stimulation of peripheral nerves have targeted nerve trunks that are less rich in or devoid of synaptic structures.

Provided herein are techniques for neuromodulation based on direct and focused modulation of targeted region(s) of interest and to cause targeted physiological outcome(s) as a result of the neuromodulation. Neuromodulation of the targeted region(s) of interest permits a limited and nonablative application of energy to only the targeted region(s) of interest without applying energy outside of the targeted region(s) of interest. By applying energy to a volume of tissue that includes synapses, desired outcomes may be achieved by preferentially activating the synapses to cause a release of neurotransmitters or neuropeptides. In this manner, the synapses within a region of interest are activated while synapses outside the region of interest are not activated. Targeted presynaptic neuronal cells may release neurotransmitters or neuropeptides, or induce an altered release of neurotransmitters or neuropeptides in the vicinity of neighboring non-neuronal cells or neuronal cells to modulate cell activity. This may in turn lead to local effects and/or non-local (e.g., systemic) effects outside the region of interest (e.g., in a tissue or structure containing the targeted region of interest or in an organ, tissue, or structure that does not contain the targeted region of interest) without direct stimulation of synapse-rich regions.

Neuromodulation may be used for the treatment of glucose metabolism and associated disorders, the alteration of disease progression, and the control of systemic inflammation. For example, liver modulation at one or more regions of interest may be used to treat diabetes (i.e., type 1 or type 2 diabetes), hyperglycemia, sepsis, trauma, infection, diabetes-associated dementia, obesity, or other eating or metabolic disorders. Neuromodulation may also be used to promote weight loss, control appetite, treat cachexia, or increase appetite. For example, direct pancreatic stimulation may result in increased appetite, direct liver stimulation may cause a decrease in neuropeptide Y (NPY), which in turn promotes signals of satiety, and direct spleen stimulation may result in a reduction in systemic inflammation. Further, neuromodulation of peripheral nerve ganglia may modulate the cholinergic anti-inflammatory pathway (CAP), dopamine production pathways, and glucose regulatory and/or insulin production pathways.

Neuromodulation to targeted region(s) of interest may yield treatment results that persist beyond the time of treatment. For example, a treatment of repeated energy applications to targeted region(s) of interest over a predefined period of time may yield persistent improvement in disease symptoms. The predefined period of time may be a time window of hours, days, weeks, or months within which the neuromodulation treatment occurs. Additionally, the neuromodulation treatment may include one or more separate energy application events within the predefined period of time. The separate energy application events may be repeatedly administered to the same region of interest within the predefined period of time. For example, the neuromodulation treatment may occur once daily, every other day, every two days, every three days, once weekly, or any other suitable treatment rate at a region of interest within the predefined period of time according to preset modulation parameters.

For example, the modulation parameters may include various stimulation time patterns, ranging from continuous to intermittent. The modulation parameters may also include a frequency and a duration of a stimulation application. The application frequency may be continuous or delivered at various time periods, for example, within a day or week. The treatment duration may last over various time periods, including, but not limited to, from a few minutes to several hours. Additionally, the modulation parameters may include a duration of a recovery period between ultrasound energy treatments. The duration of the recovery period may allow compensatory pathways of a region of interest to return to normal before restarting neuromodulation treatment.

However, continuous stimulation of synapses within a region of interest may produce undesired physiological outcomes in a subject over time. For example, a series of energy application events to a subject over a period of time (as part of a neuromodulation treatment protocol) to release certain molecules of interest (e.g., neurotransmitters or neuropeptides) may also cause a change in gene expression of cell receptors and/or channels for the molecules of interest in the subject (e.g., decreased expression level relative to a baseline before the energy application events) over the period of time. Down-regulation of gene expression may occur when a cell is overstimulated by a certain molecule for an extended period of time, and the corresponding production of the cell receptor for the molecule may decrease to compensate for the overstimulation of the cell by the molecule. As such, repetitive stimulation of synapses to release a molecule of interest within a region of interest over an extended period of time may cause down-regulation of the gene expression of corresponding cell receptors and/or channels, thereby reducing the effectiveness of subsequent energy application events over the extended period of time. Alternatively, repetitive stimulation of synapses within a tissue region may cause up-regulation of genes involved in the half-life of the neurotransmitters or neuropeptides by metabolizing, degrading, or inhibiting them. For example, butylrylcholinesterase (BCHE) is a gene that can be upregulated followed by protein translation, glycosylation, and secretion. BCHE can hydrolyze the neurotransmitter acetylcholine, has been proposed for a prognostic marker for various diseases (e.g. Obesity, metabolic syndromes, Inflammatory diseases, Malignancy), and is a prophylactic countermeasure to nerve agents and pesticides. BCHE is expressed in most tissues including the brain, liver and lymphatic tissues.

Accordingly, provided herein are techniques for determining and/or modifying one or more treatment parameters of a neuromodulation treatment to a subject such that an acute response (e.g., the release of neurotransmitters or neuropeptides) to each energy application event may be sustained while undesired chronic effects may be minimized. The treatment parameters may include a treatment period in which the neuromodulation treatment (e.g., the separate energy application events) is applied to the subject, a treatment frequency of the separate energy application events within the treatment period, and/or a duration of a recovery period (e.g., a period of time between subsequent neuromodulation treatments or treatment periods). For example, a recovery period may facilitate the reversal of any undesired physiological effects caused by the neuromodulation treatment, such as an undesired change to the level of gene expression. After the duration of the recovery period has lapsed and any change to the level of gene expression has substantially reversed (e.g., towards a baseline threshold before neuromodulation treatment), subsequent neuromodulation treatment may begin. In some embodiments, a change in the level of gene expression may be a desired effect of neuromodulation treatment of a subject. In such embodiments, if the previous neuromodulation treatment has changed (e.g., increased or decreased) the level of gene expression in the appropriate direction, a recovery period may be skipped and subsequent neuromodulation treatment may begin.

The treatment parameters (e.g., the treatment period, the treatment frequency, and the duration of the recovery period) may be determined prior to the first neuromodulation treatment to the subject. In some embodiments, the treatment parameters may be determined based on a desired physiological outcome in the subject as a result of neuromodulation treatment or historical or experimental data. After the first neuromodulation treatment has been completed, the expression level of certain genes in the subject may be assessed and a determination may be made as to whether the expression levels of the genes are desired or not. If the expression levels of the genes are desired, subsequent neuromodulation treatment may proceed based on the previously determined treatment parameters. If the expression levels of the genes are not desired, the treatment parameters for subsequent neuromodulation may be altered based on factors including, but not limited to, the assessed expression levels of the genes in the subject, the desired physiological outcome in the subject, historical data, or experimental data. As such, the neuromodulation techniques provided herein may optimize the treatment parameters of neuromodulation treatment of a subject over an extended period of time such that a desired acute response to the neuromodulation treatment may be maintained while any undesired chronic effects of the neuromodulation treatment may be minimized.

To that end, the disclosed neuromodulation techniques may be used in conjunction with a neuromodulation system. FIG. 1 is a schematic representation of a system 10 for neuromodulation to achieve neurotransmitter release and/or to activate components (e.g., the presynaptic cell, the postsynaptic cell) of a synapse in response to an application of energy. The depicted system includes a pulse generator 14 coupled to an energy application device 12 (e.g., an ultrasound transducer). The energy application device 12 is configured to receive energy pulses (e.g., via one or more leads or a wireless connection) and direct the energy pulses to a region of interest (e.g., a peripheral nerve ganglion, or a portion thereof), which in turn results in a targeted physiological outcome. In certain embodiments, the pulse generator 14 and/or the energy application device 12 may be implanted at a biocompatible site (e.g., the abdomen), and the lead(s) couple the energy application device 12 and the pulse generator 14 internally. For example, the energy application device 12 may be a MEMS transducer, such as a capacitive micromachined ultrasound transducer.

In certain embodiments, the energy application device 12 and/or the pulse generator 14 may communicate wirelessly, for example with a controller 16 that may in turn provide instructions to the pulse generator 14. In other embodiments, the pulse generator 14 may be an extracorporeal device (e.g., may operate to apply energy transdermally or in a noninvasive manner from a position outside of a subject's body), and may, in certain embodiments, be integrated within the controller 16. In embodiments in which the pulse generator 14 is extracorporeal, the energy application device 12 may be operated by a caregiver and positioned at a spot on or above a subject's skin such that the energy pulses are delivered transdermally to a desired internal tissue. Once positioned to apply energy pulses to the desired site, the system 10 may initiate neuromodulation to achieve a targeted physiological outcome or clinical effects.

In certain embodiments, the system 10 may include an assessment device 20 that is coupled to the controller 16 and is configured to assess characteristics indicative of whether the targeted physiological outcome of the modulation has been achieved. In one embodiment, the targeted physiological outcome may be local. For example, the modulation may result in changes to the local tissue or changes in function, such as tissue structure changes, a local change in concentration of certain molecules, tissue displacement, increased fluid movement, etc.

In certain embodiments, the modulation may result in systemic and/or non-local changes. The targeted physiological outcome may relate to a change in concentration of circulating molecules or a change in a characteristic of a tissue that does not include the region of interest to which energy was directly applied. In one example, the displacement may be a proxy measurement for a desired modulation, and displacement measurements below an expected displacement value may result in modification of modulation parameters until an expected displacement value is induced. Accordingly, the assessment device 20 may be configured to assess concentration changes in some embodiments. In some embodiments, the assessment device 20 may be an imaging device configured to assess changes in tissue size and/or position. While the depicted elements of the system 10 are shown separately, it should be understood that some or all of the elements may be combined with one another. Further, some or all of the elements may communicate in a wired or wireless manner with one another.

Based on the assessment, the modulation parameters of the controller 16 may be altered. For example, if a desired modulation is associated with a change in concentration (e.g., circulating concentration or tissue concentration of one or more molecules) within a defined time window (e.g., 5 minutes or 30 minutes after a procedure of energy application starts) or relative to a baseline at the start of a procedure, a change of the modulation parameters (e.g., pulse frequency) may be desired, which in turn may be provided to the controller 16, either by an operator or via an automatic feedback loop, for defining or adjusting the energy application parameters or modulation parameters of the pulse generator 14.

The system 10 as provided herein may provide energy pulses according to various modulation parameters. For example, the modulation parameters may include various stimulation time patterns, ranging from continuous to intermittent. With intermittent stimulation, energy is delivered for a period of time at a certain frequency during a signal-on time. The signal-on time is followed by a period of time with no energy delivery, referred to as signal-off time. The modulation parameters may also include frequency and duration of a stimulation application. The application frequency may be continuous or delivered at various time periods, for example, within a day or week. The treatment duration may last over various time periods, including, but not limited to, from a few minutes to several hours. In certain embodiments, treatment duration with a specified stimulation pattern may last for one hour, repeated at, for example, 72 hour intervals. In certain embodiments, treatment may be delivered at a higher frequency, such as three hours, or for shorter durations, for example, thirty minutes. Thus, the application of energy, in accordance with modulation parameters, such as the treatment duration and frequency, may be adjustably controlled to achieve a desired result.

In certain embodiments, modulation parameters of the controller 16 may be altered based on one or more characteristics of a disease of a subject to achieve a desired result. The treatment duration and/or the application frequency of the application of energy may increase or decrease based on the progression of a disease over time to achieve a desired result of the treatment. For example, if the disease state of a patient worsens, the treatment duration and/or the application frequency may increase over time to achieve the desired result. In another example, if the disease state of a patient improves, the treatment duration and/or the application frequency may be maintained or decrease over time.

Figure 2:
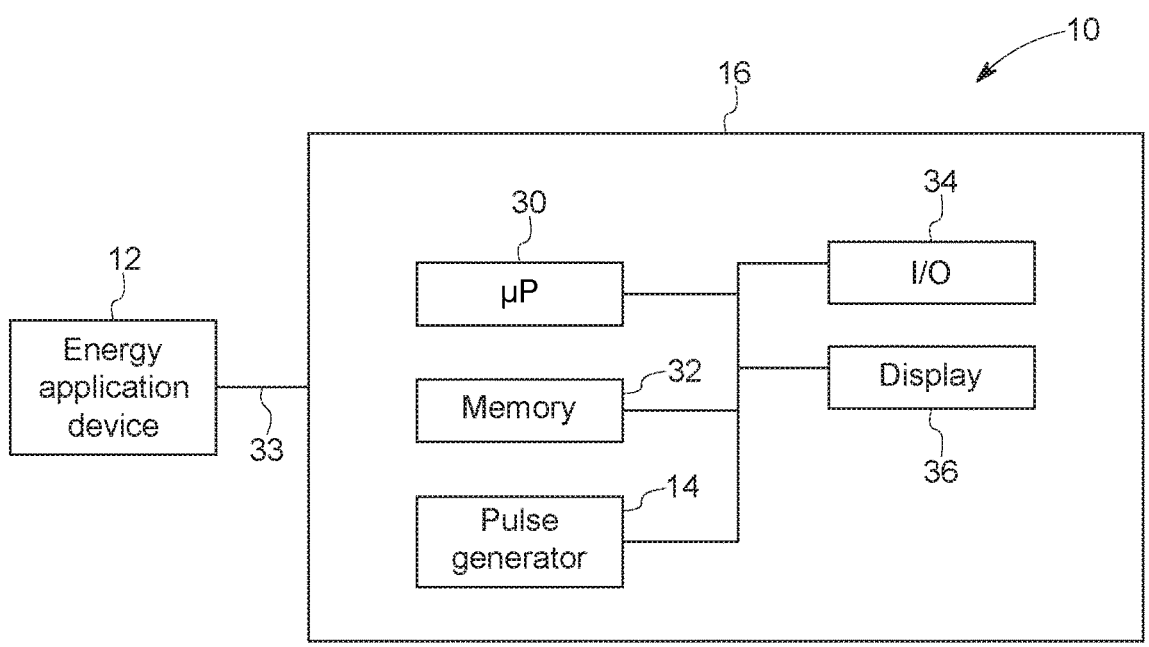
FIG. 2 is a block diagram of a neuromodulation system according to embodiments of the disclosure.

FIG. 2 is a block diagram of certain components of the system 10. As provided herein, the system 10 for neuromodulation may include a pulse generator 14 that is adapted to generate a plurality of energy pulses for application to a tissue of a subject. The pulse generator 14 may be separate or may be integrated into an external device, such as a controller 16. The controller 16 includes a processor 30 for controlling the device. Software code or instructions are stored in memory 32 of the controller 16 for execution by the processor 30 to control the various components of the device. The controller 16 and/or the pulse generator 14 may be connected to the energy application device 12 via one or more leads 33 or wirelessly.

The controller 16 also includes a user interface with input/output circuitry 34 and a display 36 that are adapted to allow a clinician to provide selection inputs or modulation parameters to modulation programs. Each modulation program may include one or more sets of modulation parameters including pulse amplitude, pulse width, pulse frequency, etc. The pulse generator 14 modifies its internal parameters in response to control signals from the controller 16 to vary stimulation characteristics of energy pulses transmitted through lead 33 to a subject to which the energy application device 12 is applied. Any suitable type of pulse generating circuitry may be employed, including but not limited to, constant current, constant voltage, multiple-independent current or voltage sources, etc. The energy applied is a function of the current amplitude and pulse width duration. The controller 16 permits adjustably controlling the energy by changing the modulation parameters and/or initiating energy application at certain times, cancelling energy application at certain times, or suppressing energy application at certain times. In one embodiment, the adjustable control of the energy application device is based on information about a concentration of one or more molecules in the subject (e.g., a circulating molecule). If the information is from the assessment device 20, a feedback loop may drive the adjustable control. For example, if a circulating glucose concentration, as measured by the assessment device 20, is above a predetermined threshold or range, the controller 16 may initiate energy application to a region of interest (e.g., a peripheral nerve ganglion) and with modulation parameters that are associated with a reduction in circulating glucose. The initiation of energy application may be triggered by the glucose concentration drifting above a predetermined (e.g., desired) threshold or outside a predefined range. In another embodiment, the adjustable control may be in the form of altering modulation parameters when an initial application of energy does not result in an expected change in a targeted physiological outcome (e.g., concentration of a molecule of interest) within a predefined time frame (e.g., 1 hour, 2 hours, 4 hours, 1 day). In certain embodiments, the assessment device 20 may be a device that measures gene expression.

In one embodiment, the memory 32 stores different operating modes that are selectable by the operator. For example, the stored operating modes may include instructions for executing a set of modulation parameters associated with a particular treatment site (e.g., the liver, the spleen, peripheral ganglion, or the pancreas). Different sites may have different associated modulation parameters. Rather than having the operator manually input the modes, the controller 16 may be configured to execute the appropriate instruction based on the selection. In another embodiment, the memory 32 stores operating modes for different types of treatment. For example, activation may be associated with a different stimulating pressure or frequency range relative to those associated with depressing or blocking tissue function. In a specific example, when the energy application device is an ultrasound transducer, the time-averaged power (temporal average intensity) and peak positive pressure are in the range of 1 mW/cm$^2$ to 30,000 mW/cm$^2$ (temporal average intensity) and 0.1 MPa to 7 MPa (peak pressure). In one example, the temporal average intensity is less than 35 W/cm$^2$ in the region of interest to avoid levels associated with thermal damage and ablation or cavitation. In another specific example, when the energy application device is a mechanical actuator, the amplitude of vibration is in the range of 0.1 to 10 mm. The selected frequencies may depend on the mode of energy application (e.g., an ultrasound actuator or a mechanical actuator).

In another embodiment, the memory 32 stores a calibration or setting mode that permits adjustment or modification of the modulation parameters to achieve a desired result. In one example, the stimulation starts at a lower energy parameter and increases incrementally, either automatically or upon receipt of an operator input. In this manner, the operator may achieve tuning of the induced effects as the modulation parameters are being changed.

The system may also include an imaging device that facilitates focusing the energy application device 12. In certain embodiments, the imaging device may be integrated with the energy application device 12 or the imaging device may be the same device as the energy application device 12 such that different ultrasound parameters (e.g., frequency, aperture, or energy) are applied for selecting (e.g., spatially selecting) a region of interest and for focusing energy to the selected region of interest for targeting and subsequent neuromodulation. In another embodiment, the memory 32 stores one or more targeting or focusing modes that is used to spatially select the region of interest within an organ or tissue structure. Spatial selection may rely on image data as provided herein. Based on the spatial selection, the energy application device 12 may be focused on the selected volume in a patient corresponding to the region of interest. For example, the energy application device 12 may be configured to first operate in the targeting mode to apply a targeting mode energy that is used to capture image data to be used for identifying the region of interest. The targeting mode energy is not at levels and/or applied with modulation parameters suitable for preferential activation. However, once the region of interest is identified, the controller 16 may then operate in a treatment mode according to the modulation parameters associated with preferential activation.

The controller 16 may also be configured to receive inputs related to the targeted physiological outcomes as an input to the selection of the modulation parameters. For example, when an imaging modality is used to assess a tissue characteristic that is a result of energy application to a region of interest, the controller 16 may be configured to receive a calculated index or parameter of the characteristic. Based on whether the index or parameter is above or below a predefined threshold, the modulation parameters may be modified. In one embodiment, the parameter can be a measure of tissue displacement of the affected tissue or a measure of depth of the affected tissue. Other parameters may include assessing a concentration of one or more molecules of interest (e.g., assessing one or more of a change in concentration relative to a threshold or a baseline/control, a rate of change, determining whether concentration is within a desired range). Further, the energy application device 12 (e.g., an ultrasound transducer) may operate under control of the controller 16 to (1) acquire image data of that may be used to spatially select a region of interest within the body, (2) apply the modulating energy to the region of interest, and (3) acquire image data to determine that the targeted physiological outcome has occurred (e.g., via displacement measurement). In such an embodiment, the imaging device, the assessment device 20 and the energy application device 12 may be the same device.

In another implementation, a desired modulation parameter set may also be stored by the controller 16. In this manner, subject-specific parameters may be determined. Further, the effectiveness of such parameters may be assessed over time. If a particular set of parameters is less effective over time, the subject may be developing insensitivity/tolerance to the activated pathways or the treatment parameters. If the system 10 includes an assessment device 20, the assessment device 20 may provide feedback to the controller 16. In certain embodiments, the feedback may be received from a user or an assessment device 20 indicative of a characteristic of the target physiological outcome. The controller 16 may be configured to cause the energy application device to apply the energy according to modulation parameters and to dynamically adjust the modulation parameters based on the feedback. For example, based on the feedback, the processor 16 may automatically alter the modulation parameters (e.g., the frequency, the amplitude, or the pulse width of an ultrasound beam or a mechanical vibration) in real time and responsive to feedback from the assessment device 20.

For example, application of energy to a region of interest according to the disclosed techniques may be used as part of a treatment protocol with the desired outcome to maintain circulating glucose concentration at predetermined concentrations, such as under about 200 mg/dL and/or over approximately 70 mg/dL. The techniques may be used to maintain glucose in a range between about 4 mmol/L to 8 mmol/L or about 70 to 150 mg/dL. The techniques may be used to maintain a normal blood glucose range for the subject (e.g., a patient), where the normal blood glucose range may be an individualized range based on the patient's individual factors such as weight, age, and/or clinical history. Accordingly, the application of energy to one or more regions of interest may be adjusted in real time based on the desired end concentration of the molecule of interest and may be adjusted in a feedback loop based on input from an assessment device 20. For example, if the assessment device 20 is a circulating glucose monitor or a blood glucose monitor, the real-time glucose measurements may be used as input to the controller 16. As provided herein, the treatment protocol (a series of regularly or irregularly spaced energy application events) may be implemented, and the circulating glucose concentration may be assessed over the course of the treatment. In one embodiment, the patient is hyperglycemic at the start of treatment, but the implementation of the treatment protocol decreases the concentration of circulating glucose and maintains the concentration within a desired range for a period of time (e.g., one month). After the period of time, the circulating glucose concentration may begin to creep up, even with regular energy application events applied according to the treatment protocol. When the circulating glucose concentration is no longer within the desired range, the treatment recovery period may be implemented until such time that the patient is once again responsive to the treatment protocol.

In another embodiment, the present techniques may be used to induce a characteristic profile of physiological changes. For example, the characteristic profile may include a group of molecules of interest that increase in concentration in the tissue and/or blood as a result of the energy application and another group of molecules of interest that decrease in concentration in the tissue and/or blood as a result of the energy application. The characteristic profile may also include a group of molecules that do not change as a result of the energy application. The characteristic profile may define concurrent changes that are associated with a desired physiological outcome. For example, the profile may include a decrease in circulating glucose seen together with an increase in circulating insulin.

Figure 3:
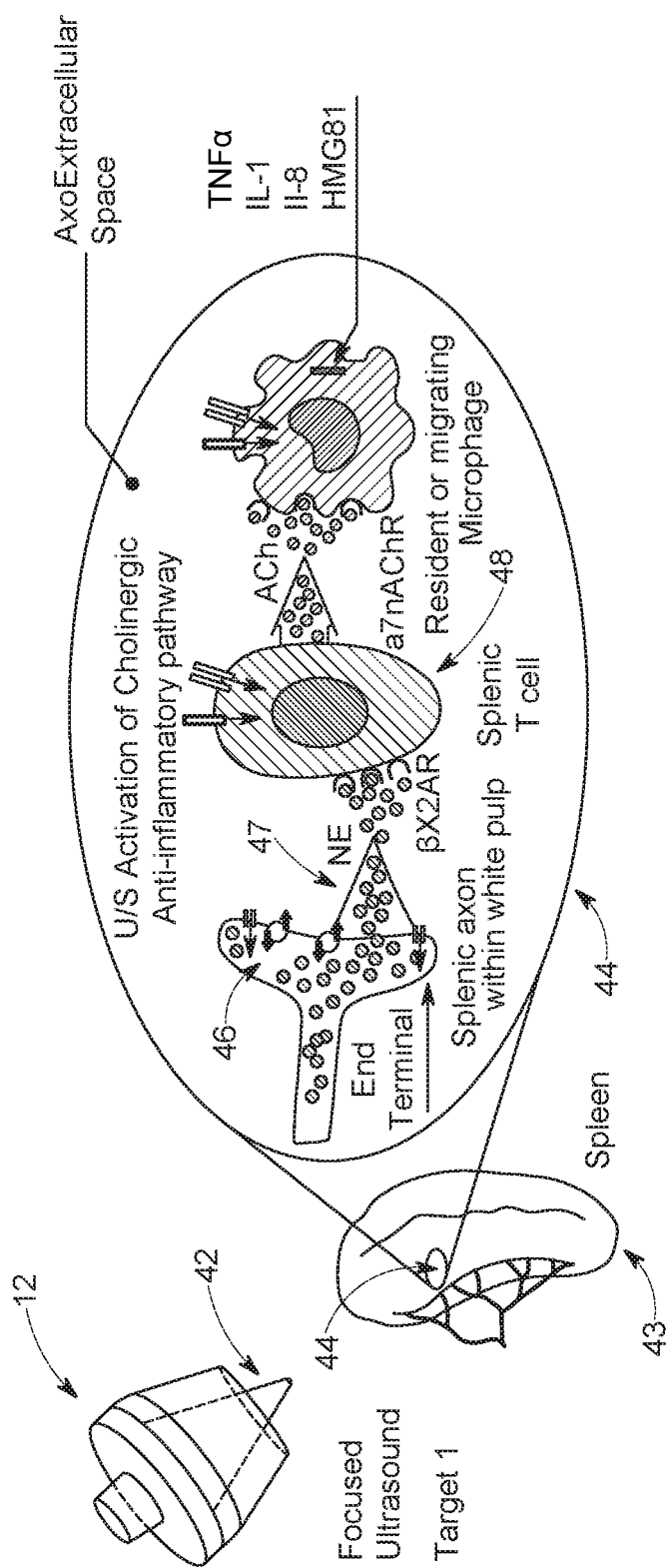
FIG. 3 is a schematic representation of an ultrasound energy application device in operation according embodiments of the disclosure.

FIG. 3 is a specific example in which the energy application device 12 includes an ultrasound transducer 42 that is capable of applying energy to a target tissue 43, shown by way of a non-limiting example as a spleen. The energy application device 12 may include control circuitry for controlling the ultrasound transducer 42. The control circuitry of the processor 30 may be integral to the energy application device 12 (e.g., via an integrated controller 16) or may be a separate component. The ultrasound transducer 42 may also be configured to acquire image data to assist with spatially selecting a desired or targeted region of interest 44 and focusing the applied energy on the region of interest 44 of the tissue 43 or structure.

The desired target tissue 43 may be an internal tissue or an organ that includes presynaptic neuronal cells having axon terminals 46 that form synapses 47 with postsynaptic cells 48 (e.g., splenic T cell). The synapses may be stimulated by direct application of energy to the axon terminals 46 within a field of focus of the ultrasound transducer 42 focused on a region of interest 44 of the target tissue 43 to cause release of molecules into the synaptic space 47. In the depicted embodiment, the axon terminal 46 forms a synapse with a splenic T cell, and the release of neurotransmitters in the synaptic space 47 and/or the change in ion channel activity in turn causes downstream effects such as the activation of the cholinergic anti-inflammatory pathway (CAP). The region of interest may be selected to include a certain type of axon terminal 46, such as an axon terminal 46 of a particular neuron type and/or one that forms a synapse with a certain type of non-neuronal cell. Accordingly, the region of interest 44 may be selected to correspond to a portion of the target tissue 43 with the desired axon terminals 46 (and associated non-neuronal cells 48). In certain embodiments, the energy application may be selected to preferentially trigger a release of one or more molecules (e.g., neurotransmitters or neuropeptides) from the nerve within the synapse. In certain embodiments, the energy application may be selected to preferentially trigger a release of one or more molecules (e.g., neurotransmitters or neuropeptides) by directly activating a neuronal cell in the region of interest 44 through direct energy transduction (i.e., mechanotransduction or voltage-activated proteins within the non-neuronal cells). In certain embodiments, the energy application may be selected to preferentially trigger a release of one or more molecules (e.g., neurotransmitters or neuropeptides) by causing an activation within neuronal cells within the region of interest 44 that elicits a desired physiological effect.

In certain embodiments, the energy may be focused or concentrated within a volume of less than about 25 mm$^3$. In certain embodiments, the energy may be focused or concentrated within a volume of about 0.5 mm$^3$ to 50 mm$^3$. A focal volume and a focal depth for focusing or concentrating the energy within the region of interest 44 may be influenced by the size or the configuration of the energy application device 12. The focal volume of the energy application may be defined by the field of focus of the energy application device 12. As provided herein, the energy may be substantially applied only to the region or the region(s) of interest 44 to preferentially activate the spleen 43. Accordingly, only a subset of a plurality of axon terminals 46 within the spleen 43 are exposed to the direct energy application.

The region(s) of interest 44 containing the axons 46 may be identified by imaging, reference to anatomical landmarks, etc., to perform the spatial selection. The region of interest 44 in the target tissue 43 may be selected based on factors including, but not limited to, historical or experimental data (e.g., data showing an association of a particular location with a desired or targeted physiological outcome). Alternatively or additionally, the system 10 may apply energy to individual axon terminals 46 until the desired targeted physiological effect is achieved. It should be understood that the spleen 43 is by way of example only. The disclosed selection of axon terminals 46 for preferential activation via a direct energy application to a region of interest 44 using spatial information of visualized nerves may be used in conjunction with other organs or structures (e.g., liver, pancreas, gastrointestinal tissue, or peripheral nerve ganglia).

In other embodiments, the region(s) of interest may be identified by the presence or the absence of one or more biological markers. Such markers may be assessed by staining tissue and obtaining images indicative of the stain to identify regions of the tissue that include the biological marker(s). In some embodiments, the biological marker information may be obtained by in vivo staining technologies to obtain location data of the biological marker(s) within the subject in real time. In other embodiments, the biological marker information may be obtained by in vitro staining technologies to obtain location data from one or more representative images that is used to predict the locations of the biological marker(s) within the subject. In some embodiments, the region of interest is selected to correspond with tissue that is rich in a particular biological marker or that lack a particular biological marker. For example, the one or more biological markers may include markers for neuronal structures (e.g., myelin sheath markers).

The region of interest in the organ or tissue may be spatially selected based on operator input. For example, an operator may designate the region of interest on an acquired image by directly manipulating the image (e.g., drawing or writing the region of interest on the image) or by providing image coordinate information that corresponds to the region of interest. In another embodiment, the region of interest may be automatically selected based on the image data to achieve spatial selection. In some embodiments, the spatial selection includes storing data related to the region of interest in a memory and accessing the data.

The assessment of neuromodulation effects may be used as an input or a feedback for selecting or modifying neuromodulation parameters. Assessment techniques may use direct assessments of tissue condition or function as the targeted physiological outcomes. The assessment may occur before (i.e., baseline assessment), during, and/or after the neuromodulation. The assessment techniques may include at least one of: functional magnetic resonance imaging, diffusion tensor magnetic resonance imaging, positive emission tomography, or acoustic monitoring, thermal monitoring. The assessment techniques may also include nucleic acid, protein and/or marker concentration assessment. The images from the assessment techniques may be received by the system for automatic or manual assessment. Based on the image data, the modulation parameters may be modified. For example, a change in tissue size or displacement may be utilized as a marker of local neurotransmitter concentration, and used as a surrogate marker for exposure of local cells to phenotype modulating neurotransmitters, and effectively as a marker of a predicted effect on glucose metabolic pathways or systemic inflammation pathways. The local concentration may refer to a concentration within a field of focus of the energy application.

Additionally or alternatively, the system may assess the presence or concentration of one or more molecules in a tissue region or in the blood. Tissue may be acquired by a fine needle aspirate, and the assessment of the presence or levels of molecules of interest (e.g., metabolic molecules, markers of metabolic pathways, peptide transmitters, catecholamines, cholinesterase) may be performed by any suitable technique known to one of ordinary skilled in the art.

In other embodiments, the targeted physiological outcomes may include, but are not limited to, tissue displacement, tissue size changes, a change in concentration of one or more molecules (e.g., local, non-local, or circulating concentration), a change in gene or marker expression, afferent activity, and cell migration, etc. For example, tissue displacement may occur as a result of energy application to the tissue. By assessing the tissue displacement (e.g., via imaging), other effects may be estimated. For example, a certain displacement may be characteristic of a particular change in molecule concentration. In one example, a 5% tissue displacement (e.g., liver displacement) may be indicative of or associated with a desired reduction in circulating glucose concentration based on empirical data. In another example, the tissue displacement may be assessed by comparing reference image data (tissue image before application of energy to the tissue) to post-treatment image data (tissue image taken after application of energy to the tissue) to determine a maximum or average displacement value of the tissue. If the displacement is greater than a threshold displacement, the application of energy may be assessed as likely to have caused the desired targeted physiological outcome.

Figure 4:
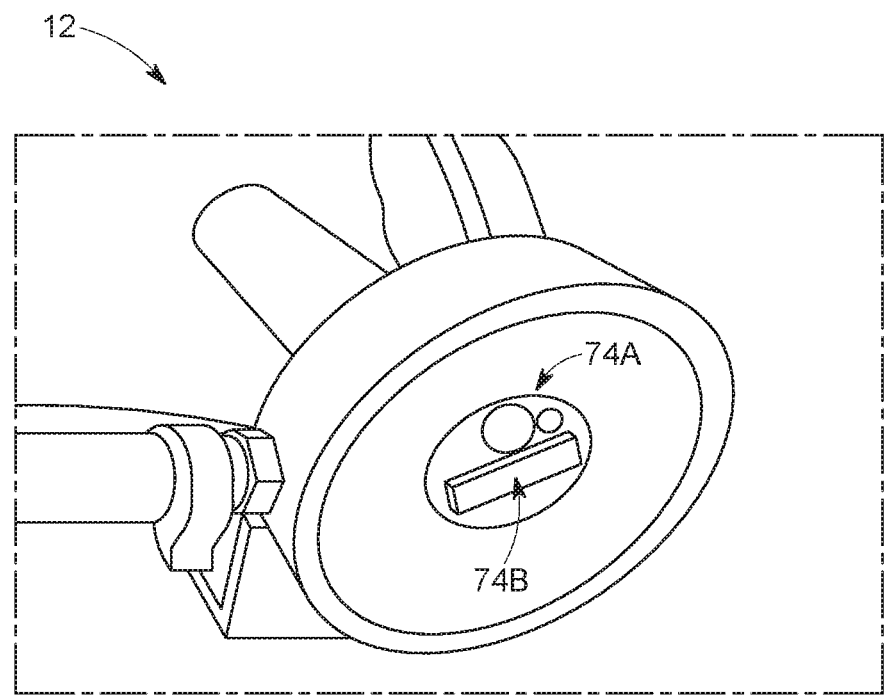
FIG. 4 is an example of an energy application device that may be used in conjunction with the neuromodulation system of FIG. 1 according to embodiments of the disclosure.

FIG. 4 is an example of an energy application device 12 that may be used in conjunction with the system 10 of FIG. 1 including a high intensity focused ultrasound (HIFU) transducer 74A and an imaging ultrasound transducer 74B arranged in a single energy application device 12 that may be controlled (e.g., by the controller 16) to apply energy and to image the target tissue as provided herein.

Figure 5:
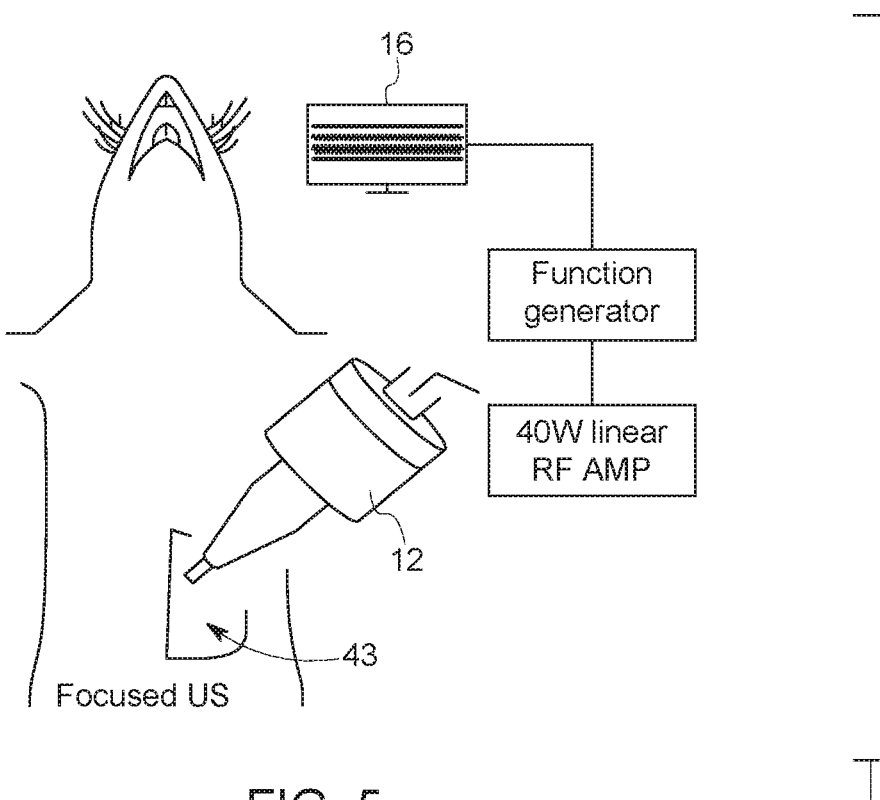
FIG. 5 is a schematic illustration of the experimental setup for ultrasound energy application to achieve target physiological outcomes according to embodiments of the disclosure.

FIG. 5 shows an experimental setup used to perform certain neuromodulation experiments focused on a target tissue 43 (e.g., a spleen, a liver, a pancreas, gastrointestinal tissue, or a peripheral nerve ganglion) as provided herein. The energy application device 12 may operate according to parameters set by the controller 16 to apply energy to a region of interest in the target tissue 43. While the depicted experimental setup is shown with a 40 W RF amplifier, this is by way of example only, and other amplifiers (e.g., linear amplifiers) may be used. In certain setups, the rat heads are inserted in a birdcage coil.

Figure 6:
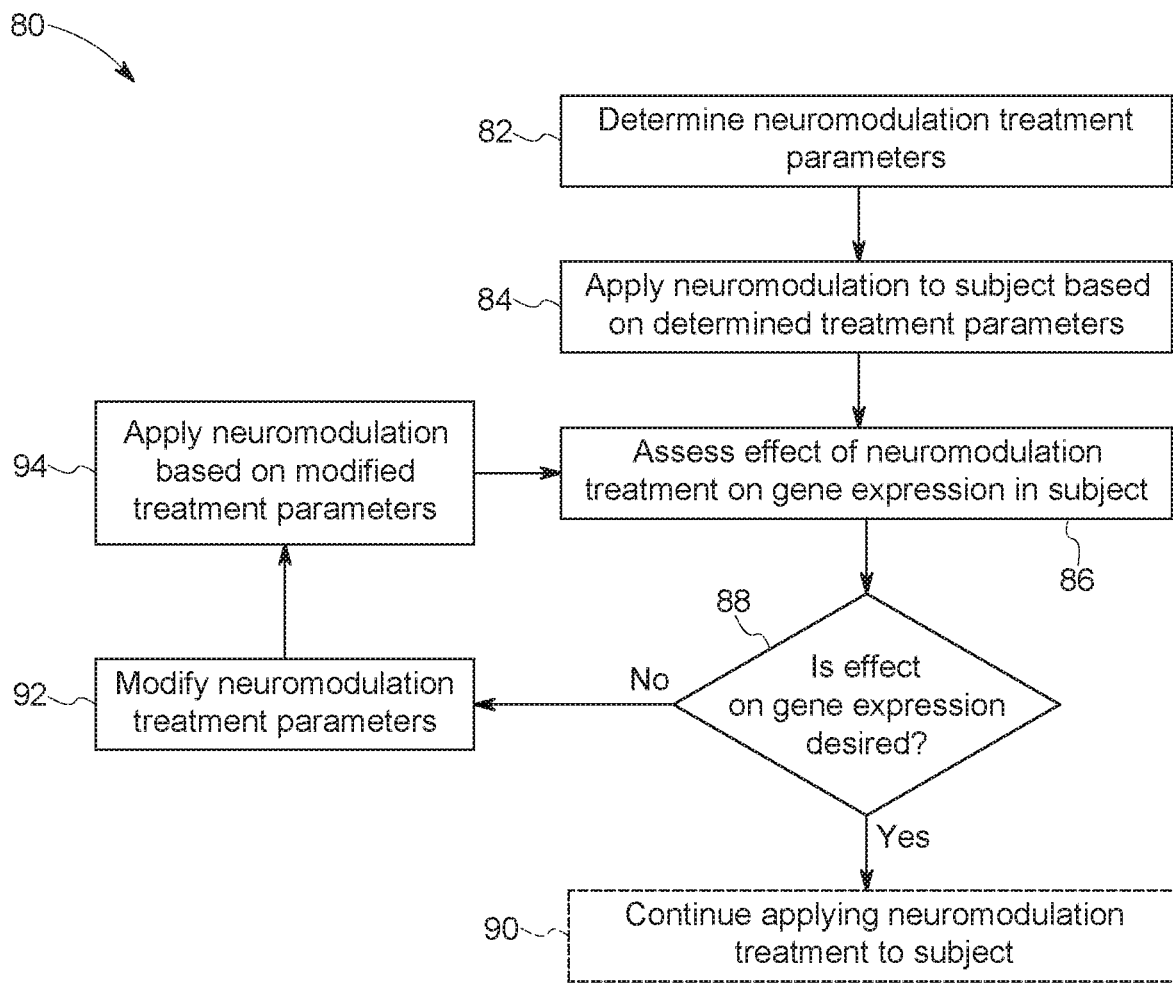
FIG. 6 is a flow diagram of a neuromodulation technique for optimizing treatment over time according to embodiments of the disclosure.

FIG. 6 is a flow diagram of a method 80 for assessing the effects of neuromodulation treatment over a period of time, which in turn may be used as an input or a feedback for selecting or modifying the treatment parameters. Although FIG. 6 is described with regard to the assessment of the effect of neuromodulation treatment on gene expression in a subject, it should be understood that the assessed effect of neuromodulation treatment may include other desired physiological effects of neuromodulation treatment in the subject or undesired physiological effects of neuromodulation treatment in the subject. In some embodiments, a characteristic profile of physiological changes induced by the neuromodulation treatment may be assessed in FIG. 6.

As provided herein, the assessment of whether the patient is responsive to the treatment protocol may be based on a characteristic profile. The characteristic profile may define concurrent changes, relative to a baseline profile assessed before the treatment protocol is implemented, that are associated with a desired physiological outcome. For example, the characteristic profile may include concentration information for a group of molecules of interest that increase in concentration in the tissue and/or blood as a result of the neuromodulation treatment, another group of molecules of interest that decrease in concentration in the tissue and/or blood as a result of the neuromodulation treatment, and/or a group of molecules that do not change as a result of the neuromodulation treatment. The characteristic profile may include expression information for a group of genes that increase in expression as a result of the neuromodulation treatment, another group of genes that decrease in expression as a result of the neuromodulation treatment, and/or a group of genes that do not change in expression as a result of the neuromodulation treatment. Alternatively or additionally, the characteristic profile may reflect changes in the activation or modification state of certain proteins, e.g., phosphorylation, acetylation, relative to baseline.

In the method 80, one or more neuromodulation treatment parameters in the treatment protocol may be selected or determined in step 82. In certain embodiments, the treatment parameters may be selected or determined based on a desired physiological outcome in the subject. The treatment parameters may include a treatment period in which the neuromodulation treatment (e.g., the separate energy application events) is applied to the subject. For example, the treatment period of a subject may occur over three days, five days, one week, one and half weeks, two weeks, or any other suitable period of time to achieve a desired physiological outcome in the subject. The treatment parameters may also include a treatment frequency of the separate energy application events to a subject within the treatment period. For example, the treatment frequency may be twice daily, once daily, four times a week, three times a week, two times a week, once a week, or any other suitable frequency of energy application events to achieve a desired physiological outcome in the subject. Further, the treatment parameters may include a treatment recovery period (e.g., a period of time between subsequent neuromodulation treatments or treatment periods). The duration of the recovery period may facilitate the reversal of any undesired physiological effects caused by the neuromodulation treatment. For example, the duration of the recovery period may allow the expression level of particular genes to return to a level of expression similar to a baseline threshold before neuromodulation treatment. In some embodiments, the duration of the recovery period may be one day, two days, three days, four days, five days, six days, a week, two weeks, or any other suitable period of time between a first treatment period and a second treatment period to achieve a desired physiological outcome in the subject. In certain embodiments, a duration of a recovery period may not be determined until step 88 of method 80. In some embodiments, the treatment parameters may be determined based on factors including, but not limited to, historical or experimental data (e.g., data showing an association of particular treatment parameters with a desired or targeted physiological outcome). In some embodiments, the treatment parameters may be determined based on a subject's current physiological state, clinical history, weight, or age.

In step 84, neuromodulation treatment based on the determined treatment parameters (e.g., the treatment period, the frequency, and/or the rest period) in step 82 is applied to the subject to achieve a desired physiological outcome. For example, neuromodulation treatment to a subject may include the application of energy to a target tissue of the subject's body once a day for one week. In another example, neuromodulation treatment to a subject may include the application of energy to a target tissue of the subject's body once a day for two weeks. After a single neuromodulation treatment or a series of treatments are complete, the effect of the neuromodulation treatments on the expression level of particular genes in the subject may be assessed in step 86.

For example, one or more assessment techniques for determining the expression level of particular genes of the subject may be used. The assessment techniques may generate RNA or mRNA transcriptome data from a subset of cells in the target tissue via RNA-sequencing, quantitative polymerase chain reaction (qPCR), microarrays, or other suitable techniques. In some embodiments, the particular genes for assessment may be selected or determined based on an association of the genes with a desired physiological outcome. For example, the assessed genes may produce molecules (e.g., proteins) associated with a desired pathway (e.g., cholinergic anti-inflammatory pathway) to be activated by the neuromodulation treatment. In certain embodiments, an assessment of the level of gene expression of particular genes may be performed before neuromodulation treatment of the subject begins to acquire a baseline level of gene expression for the particular genes. The assessment data may also assess the gene expression data via group-level analysis of the plurality of genes, such as clustering. Clustering techniques may be used for class discovery or categorization. A patient's characteristic profile of gene expression may be used to identify a closest match among already-categorized gene expression profiles. For example, a responsive patient may have a gene expression profile that is characteristic of the gene expression associated with treatment responsiveness, while a treatment insensitive patient may have a gene expression profile that is characteristic of the gene expression associated with treatment nonresponsiveness. Cluster analysis may be used to determine whether an uncategorized characteristic gene expression profile of a patient should be categorized as responsive or unresponsive to treatment.

In certain embodiments, one or more assessments of a change in concentration in one or more molecules of interest (e.g., glucose, neurotransmitters, neuropeptides, cholinesterases, or cytokines) may also be performed in step 86. The assessments of the change in concentration in the molecule (s) of interest may be used to determine whether the treatment parameters and/or the modulation parameters, as described herein, require modification in order to achieve the desired physiological outcome. Upon a determination that the treatment parameters and/or the modulation parameters require modification to achieve the desired physiological outcome from the neuromodulation treatment, the treatment parameters and/or the modulation parameters may be modified as described herein.

Based on the expression level of the genes as assessed in step 86, a determination of whether the effect of the neuromodulation treatment on the level of expression of particular genes of the subject is performed in step 88. Upon a determination that the effect on the expression level of the genes is desired, the method 80 may proceed to step 90, and subsequent neuromodulation treatments may be applied according to the determined treatment parameters in step 82. For example, in certain embodiments, a change in the expression level of particular genes as a result of the neuromodulation treatment may not be desired. If the expression level of the particular genes in step 86 is assessed to not have substantially changed (e.g., as compared to a baseline threshold before neuromodulation treatment), the neuromodulation treatment parameters determined in step 82 may be used in further neuromodulation treatments to the subject. In another example, in certain embodiments, a change (e.g., an increase or a decrease) to the expression level of particular genes as a result of the neuromodulation treatment may be desired. If the expression level of the particular genes in step 86 is assessed to have substantially changed (e.g., as compared to a baseline threshold before neuromodulation treatment), the neuromodulation treatment parameters determined in step 82 may be used in further neuromodulation treatments to the subject.

In step 88, upon a determination that the effect on the expression level of the genes is not desired, the method 80 may proceed to step 92, and the treatment parameters of the neuromodulation treatment may be modified based on the assessed effect on the expression level of the genes in the subject. For example, a change (e.g., an increase or a decrease) to the expression level of particular genes as a result of the neuromodulation treatment may not be desired. If the expression level of the particular genes is determined to have substantially changed (e.g., as compared to a baseline threshold before neuromodulation treatment), the neuromodulation treatment parameters may be modified (e.g., dynamically or adjustably controlled) to achieve the desired physiological outcome while minimizing an effect on gene expression in the subject. In another example, a change (e.g., an increase or a decrease) to the expression level of particular genes as a result of the neuromodulation treatment may be desired. If the expression level of the particular genes is determined to have not substantially changed (e.g., as compared to a baseline threshold before neuromodulation treatment), the neuromodulation treatment parameters may be modified (e.g., dynamically or adjustably controlled) to achieve the desired physiological outcome and the desired change in gene expression. In some embodiments, the treatment parameters may be modified based on factors including, but not limited to, historical data, experimental data, the subject's current physiological state, clinical history, weight, or age, the assessed effect on gene expression in the subject, or the desired physiological outcome in the subject.

In an embodiment, the expression level of genes is assessed to have substantially changed compared to a baseline threshold before neuromodulation treatment if an increase or a decrease in the expression level of the genes is at least a 10%, 20%, 30%, 50%, or 75% increase or decrease in the baseline threshold of the expression level of the genes. In another embodiment, the expression level of genes is assessed to have not substantially changed compared to a baseline threshold before neuromodulation treatment if the expression level of the genes is at most a 10%, 5%, 3%, 2%, 1%, or 0% increase or decrease in the baseline threshold of the expression level of the genes.

The treatment period may be modified in step 92 for any subsequent neuromodulation treatments (e.g., the separate energy application events) applied to the subject. In some embodiments, the treatment period of a subject may increase or decrease relative to the treatment period of previous neuromodulation treatments. In some embodiments, the treatment period of a subject may not be modified from the treatment period of previous neuromodulation treatments. The treatment frequency of the separate energy application events to the subject within the treatment period may be modified in step 92 for any subsequent neuromodulation treatments. In some embodiments, the treatment frequency may be increase or decrease relative to the treatment frequency of energy application events in previous neuromodulation treatments. In some embodiments, the treatment frequency may not be modified from the treatment frequency of energy application events in previous neuromodulation treatments.

The duration of a recovery period between subsequent treatment periods or neuromodulation treatments may be modified (or determined if not determined in step 82). In some embodiments, the duration of the recovery period may be determined based on the assessed effect of the neuromodulation treatment on the level of particular gene expression. For example, the duration of the recovery period may be determined to be a particular period of time based on the extent that the expression levels of a group of genes have increased and/or the expression levels of a group of genes have decreased relative to a baseline level of expression before neuromodulation treatment. In some embodiments, if a change (e.g., increase or decrease) in the expression level of particular genes is desired but not assessed, subsequent neuromodulation treatment of the subject may begin immediately without a recovery period. In some embodiments, if a change in the expression level of particular genes is assessed but not desired, a determined or modified recovery period may occur before subsequent neuromodulation treatment of the subject begins based on the extent of the change in the expression level of the genes. Additionally or alternatively, the duration of a recovery period may be determined based on factors including, but not limited to, historical or experimental data (e.g., data showing an association of particular recovery periods with a desired or targeted reversal of changes to gene expression). In some embodiments, the duration of the recovery period may be determined by assessing the level of gene expression in the subject at discrete points in time after the previous neuromodulation treatment until a determination is made that the level of gene expression has returned to normal (e.g., a baseline level of gene expression before neuromodulation treatment).

In step 94, neuromodulation treatment based on the modified treatment parameters (e.g., the treatment period, the treatment frequency, and/or the duration of the recovery period) in step 92 is applied to the subject to achieve the desired physiological outcome and the desired level of gene expression in the subject. After the neuromodulation treatment is performed, steps 86, 88, 92, and 94 may be repeated until a determination is made in step 88 that the assessed effect of the neuromodulation treatment on gene expression is desired. Upon determining that the assessed effect of the neuromodulation treatment on gene expression is desired, the modified neuromodulation treatment parameters (e.g., the treatment period, the treatment frequency, and/or the duration of the recovery period) may be used in any subsequent neuromodulation treatment applied to a subject. As such, the treatment parameters for neuromodulation treatment to a subject may be optimized to achieve a desired physiological outcome concurrently with a desired level of gene expression in a subject.

EXAMPLES

Physiological Effect Determination of Neuromodulation Treatment Over Time

Figure 7A:
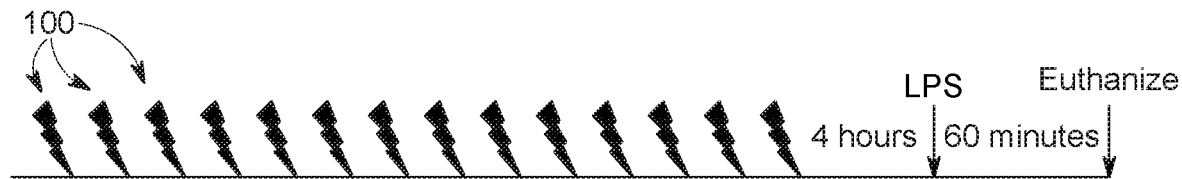
FIG. 7A is an experimental timeline of ultrasound energy application over a two week period according to embodiments of the disclosure.
Figure 7B:
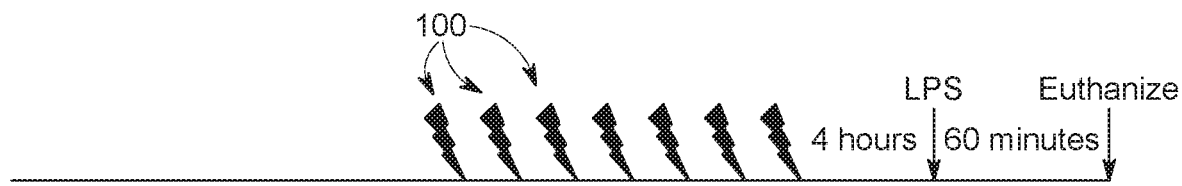
FIG. 7B is an experimental timeline of ultrasound energy application over a one week period according to embodiments of the disclosure.
Figure 7C:
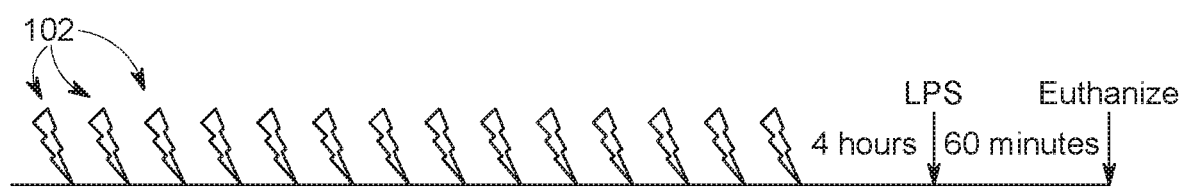
FIG. 7C is an experimental timeline of sham control application over a two week period according to embodiments of the disclosure.
Figure 7D:
FIG. 7D is an experimental timeline of a naïve control according to embodiments of the disclosure.

FIGS. 7A to 7D show an experimental timelines for neuromodulation treatment used to perform certain modulation experiments as provided herein. In FIG. 7A, ultrasound energy was applied to spleen of female Sprague Dawley (SD) rats, which were approximately 300 g and 11 weeks old at the beginning of the modulation experiments. The treatment period of the ultrasound energy application events was two weeks at a once daily treatment frequency. In FIG. 7B, ultrasound energy was also applied to the spleen of female SD rats, which were approximately 300 g and 11 weeks old at the beginning of the modulation experiments. The treatment period of the ultrasound energy application events was one week at a once daily treatment frequency. In FIGS. 7C and 7D, sham controls were performed by placing an ultrasound transducer on the spleen of female SD rats without applying the ultrasound stimulus. In FIG. 7C, the treatment period of the sham controls was two weeks at a once daily treatment frequency. In FIG. 7D, the treatment period of the sham controls was one week at a once daily treatment frequency.

In the depicted embodiments of FIGS. 7A and 7B, each ultrasound energy application event 100 was performed for 1 minute before and after a thirty second rest period. Standard anesthesia (e.g., 2% to 4% isoflurane) was used prior to each ultrasound energy application treatment. As depicted in FIGS. 7A and 7B, lipopolysaccharides (LPS) was administered to the female SD rats via intraperitoneal (IP) injection four hours after the last ultrasound energy application in the treatment period. LPS are bacterial molecules that elicit a strong immune or inflammatory response. The female SD rats were sacrificed at a time period after the LPS injection for organ harvesting and processing. While the time period shown is 1 hour after the LPS injection by way of example, it should be understood that, in other embodiments, the time period to assess induced changes may be variable.

In the depicted embodiments of FIGS. 7C and 7D, each sham control application event 102 was performed by placing an ultrasound transducer on the spleen of female SD rats without applying the ultrasound stimulus. As depicted in FIG. 7C, LPS was administered to the female SD rats via IP injection four hours after the last sham control application event in the treatment period. The female SD rats were sacrificed at a time period after the LPS injection for organ harvesting and processing. While the time period shown is 1 hour after the LPS injection by way of example, it should be understood that, in other embodiments, the time period to assess induced changes may be variable. As depicted in FIG. 7D, LPS was not administered to the female SD rats via IP injection, and the female SD rats were sacrificed at a time period after the last sham control application event in the time period. While the time period shown is 5 hours after the last sham control application event by way of example, it should be understood that, in other embodiments, the time period to assess induced changes may be variable. Spleen samples were harvested from the sacrificed female SD rats.

The effects of ultrasound stimulation over an extended period of time (e.g., once daily over a one week period, once daily over a two week period) were examined. Splenic hilum portions were obtained in order to measure the expression level of particular genes. The splenic hilum portions were treated for 24 hours in RNAlater, and stored in an RNAfree tube at −80° C. RNA was extracted from the splenic hilum portions, prepared for sequencing using TruSeq Stranded mRNA Library Prep, and sequenced for assessment of gene expression levels.

The present examples demonstrate a noninvasive method to stimulate axon terminals of neurons in a target tissue to achieve a desired physiological outcome (e.g., the release of one or more molecules of interest, such as neurotransmitters or neuropeptides), and to assess the expression level of particular genes associated directly or indirectly with the desired physiological outcome over time. The expression level of particular cytokine activity genes associated with systemic inflammation were monitored via RNA transcriptome sequencing of stimulated spleens and sham control spleens. Additionally, the blood concentrations of various systemic inflammation related cytokines and proteins were measured. After a single ultrasound energy application event (e.g., a single dose) to the spleen, ultrasound neuromodulation treatments were found to affect (e.g., increase or decrease) the concentration of particular proteins in the blood and/or the spleen. After a week of ultrasound energy application events to the spleen, ultrasound neuromodulation treatments were found to affect (e.g., increase or decrease) the concentration of particular proteins in the blood and/or the spleen but the level of gene expression in the spleen had not substantially changed (e.g., as compared to a baseline level before neuromodulation treatment). After two weeks of ultrasound energy application events to the spleen, ultrasound neuromodulation treatments were found to affect the expression level of certain genes in the spleen. Collectively, this data demonstrates that the treatment parameters of ultrasound neuromodulation treatments within target tissues or structures may be optimized such that ultrasound neuromodulation treatments may achieve a desired physiological outcome while inducing a desired expression level of particular genes within the subject based on one or more adjustable treatment parameters (e.g., a treatment period, a treatment frequency, or a duration of a recovery period between subsequent treatment periods).

Figure 8:
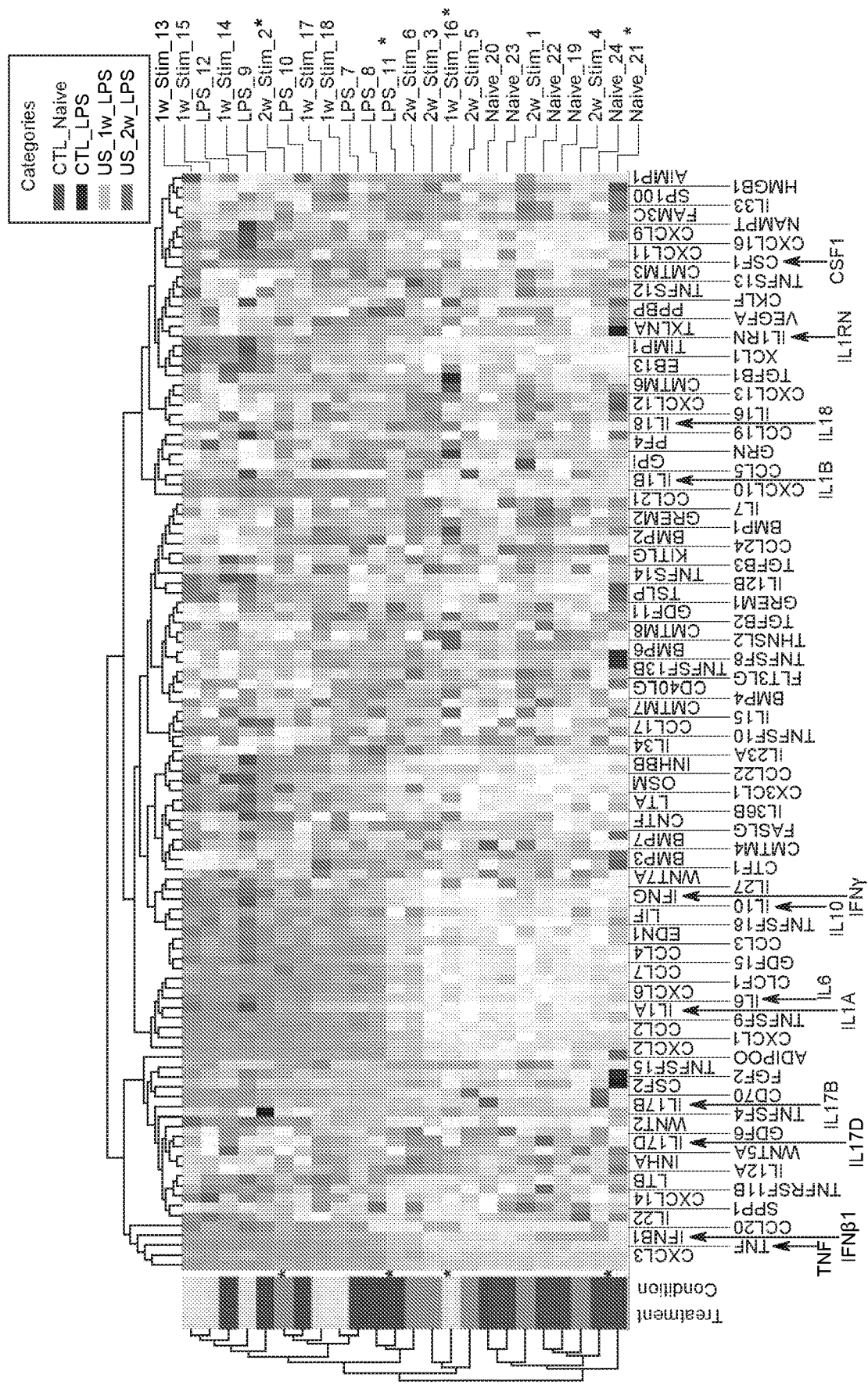
FIG. 8 shows transcriptome data of genes related to cytokine activity (Gene Ontology GO:0005125) according to embodiments of the disclosure.

FIG. 8 shows transcriptome data of particular genes related to cytokine activity in naïve rats, sham controls (i.e., rats that received LPS but not ultrasound stimulation), and rats that received LPS with ultrasound stimulation over a one week period and a two week period. The expression levels of particular cytokine activity genes (Gene Ontology GO:0005125) after a two week period of ultrasound stimulation were found to correlate with naïve expression levels of cytokine activity genes. That is, the ultrasound treatment protocol was capable of reversing the effects of LPS-induced immune response. In one embodiment, the present techniques may track expression of cytokine activity genes, the tissue or in samples taken from circulating fluid and may use expression of one or more cytokine activity genes as a proxy marker for effective neuromodulation of the spleen as part of a treatment protocol to reduce inflammation or to treat immune-associated disorders.

Figure 9A:
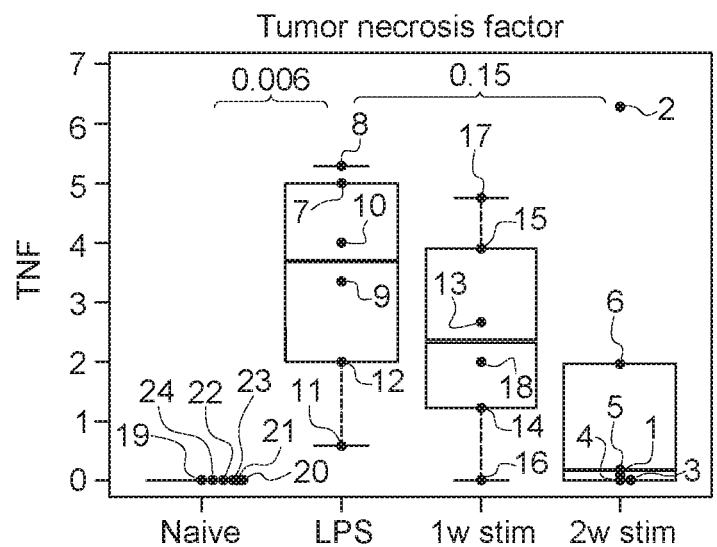
FIG. 9A shows the RNA concentration of tumor necrosis factor (TNF) in the naïve spleens, sham control spleens, and ultrasound stimulated spleens according to embodiments of the disclosure.
Figure 9B:
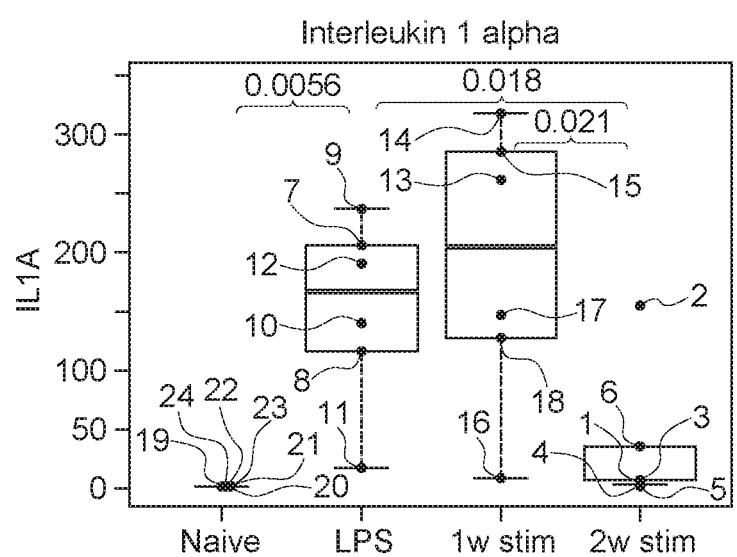
FIG. 9B shows the RNA concentration of interleukin 1 alpha in naïve spleens, sham control spleens, and ultrasound stimulated spleens according to embodiments of the disclosure.
Figure 9C:
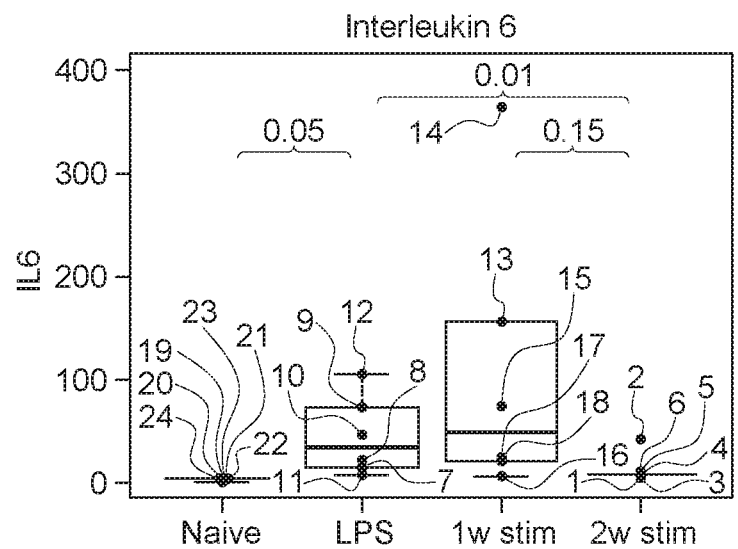
FIG. 9C shows the RNA concentration of interleukin 6 in naïve spleens, sham control spleens, and ultrasound stimulated spleens according to embodiments of the disclosure.
Figure 9D:
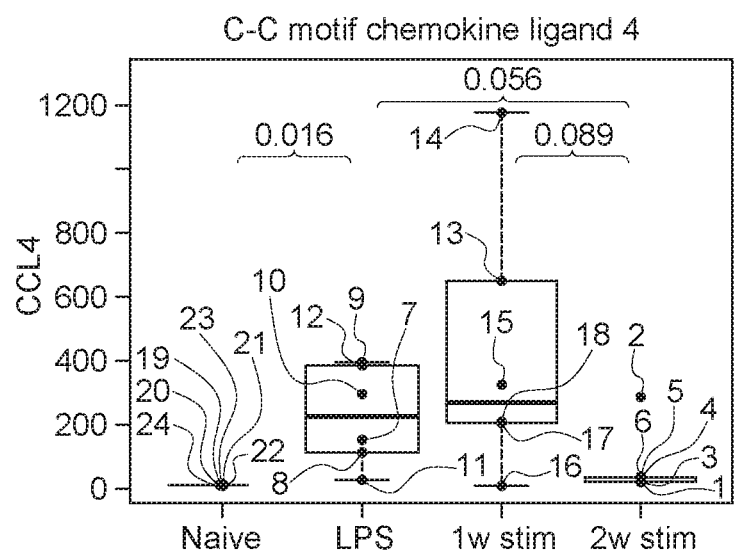
FIG. 9D shows the RNA concentration of C-C motif chemokine ligand 4 in naïve spleens, sham control spleens, and ultrasound stimulated spleens according to embodiments of the disclosure.
Figure 9E:
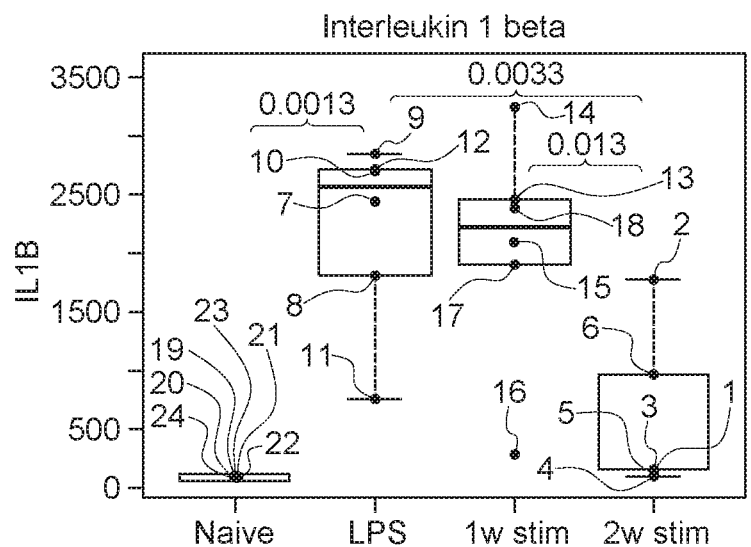
FIG. 9E shows the RNA concentration of interleukin 1 beta in naïve spleens, sham control spleens, and ultrasound stimulated spleens according to embodiments of the disclosure.
Figure 9F:
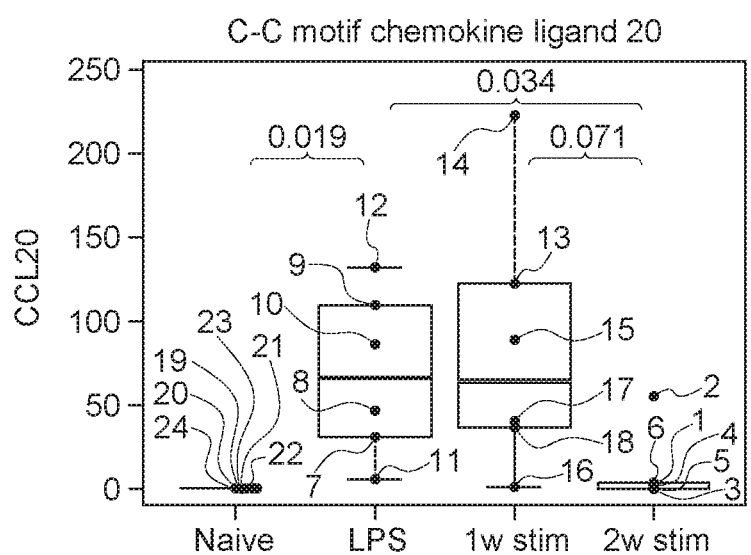
FIG. 9F shows the RNA concentration of C-C motif chemokine ligand 20 in naïve spleens, sham control spleens, and ultrasound stimulated spleens according to embodiments of the disclosure.

FIGS. 9A to 9F show the RNA concentrations of various cytokines in naïve rats, sham controls (i.e., rats that received LPS but not ultrasound stimulation), and rats that received LPS with ultrasound stimulation over a one week period and a two week period. FIG. 9A shows the concentration of tumor necrosis factor (TNF) in naïve spleens, sham control spleens, and ultrasound stimulated spleens over a one week period and a two week period. FIG. 9B shows the concentration of interleukin 1 alpha in naïve spleens, sham control spleens, and ultrasound stimulated spleens over a one week period and a two week period. FIG. 9C shows the concentration of interleukin 6 in naïve spleens, sham control spleens, and ultrasound stimulated spleens over a one week period and a two week period. FIG. 9D shows the concentration of C-C motif chemokine ligand 4 in naïve spleens, sham control spleens, and ultrasound stimulated spleens over a one week period and a two week period. FIG. 9E shows the concentration of interleukin 1 beta in naïve spleens, sham control spleens, and ultrasound stimulated spleens over a one week period and a two week period. FIG. 9F shows the concentration of C-C motif chemokine ligand 20 in naïve spleens, sham control spleens, and ultrasound stimulated spleens over a one week period and a two week period. As shown in FIGS. 9A to 9F, ultrasound stimulation over a two week period shows lower RNA concentrations of the various cytokines as compared to the concentrations of the various cytokines after a one week period of ultrasound stimulation. As such, in contrast to a one week period of ultrasound stimulation, a two week period of ultrasound stimulation may alter levels of gene expression.

Figure 10A:
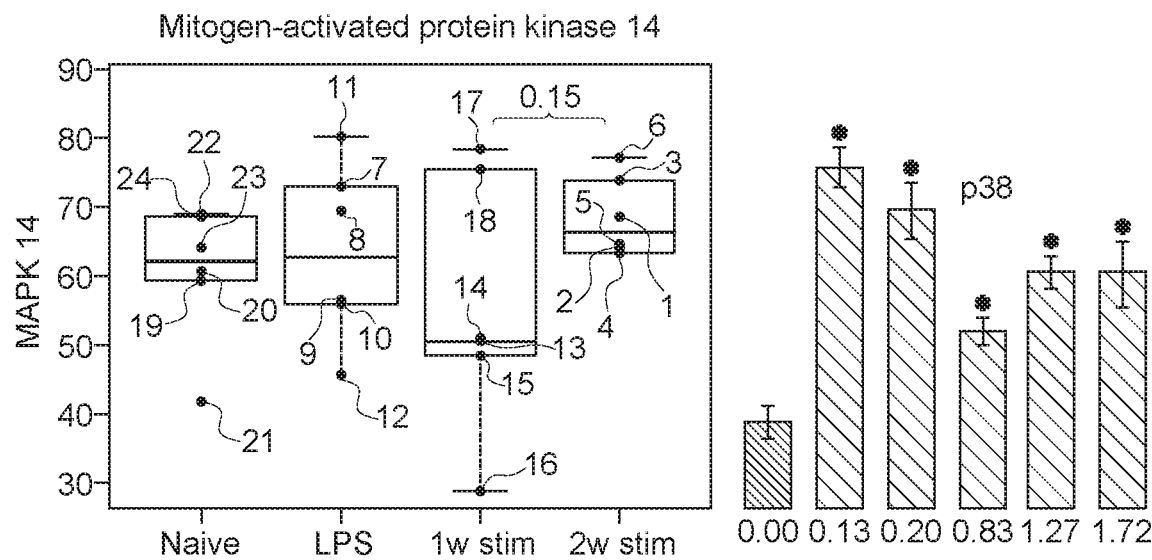
FIG. 10A shows the RNA and protein concentration of mitogen-activated protein kinase 14 (p38) in naïve spleens, sham control spleens, and ultrasound stimulated spleens according to embodiments of the disclosure.
Figure 10B:
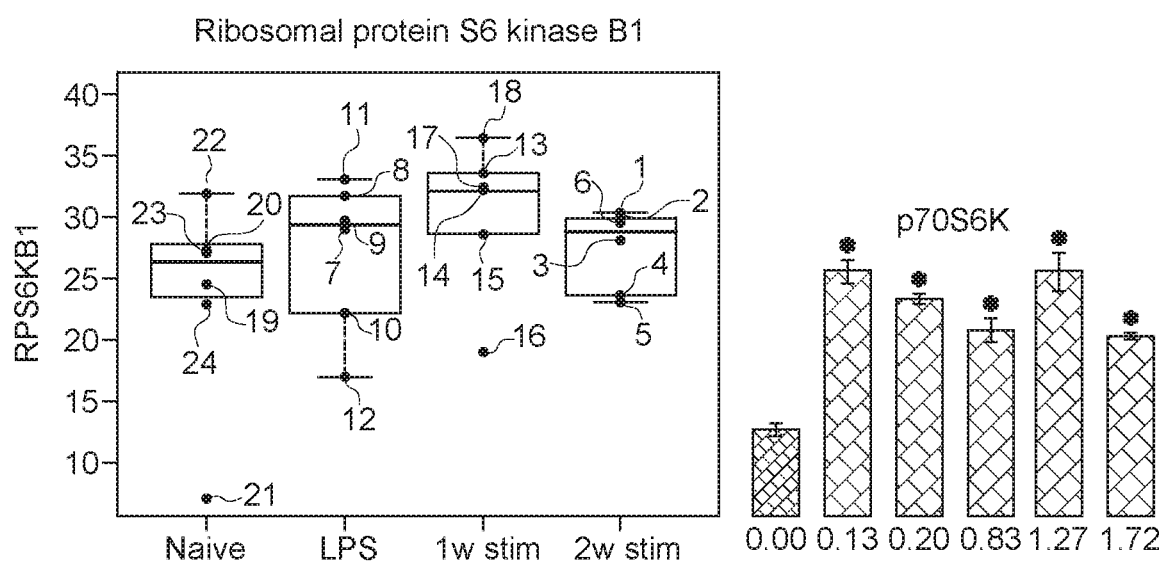
FIG. 10B shows the RNA and protein concentration of ribosomal protein S6 kinase B1 (p70S6K) in naïve spleens, sham control spleens, and ultrasound stimulated spleens according to embodiments of the disclosure.
Figure 10C:
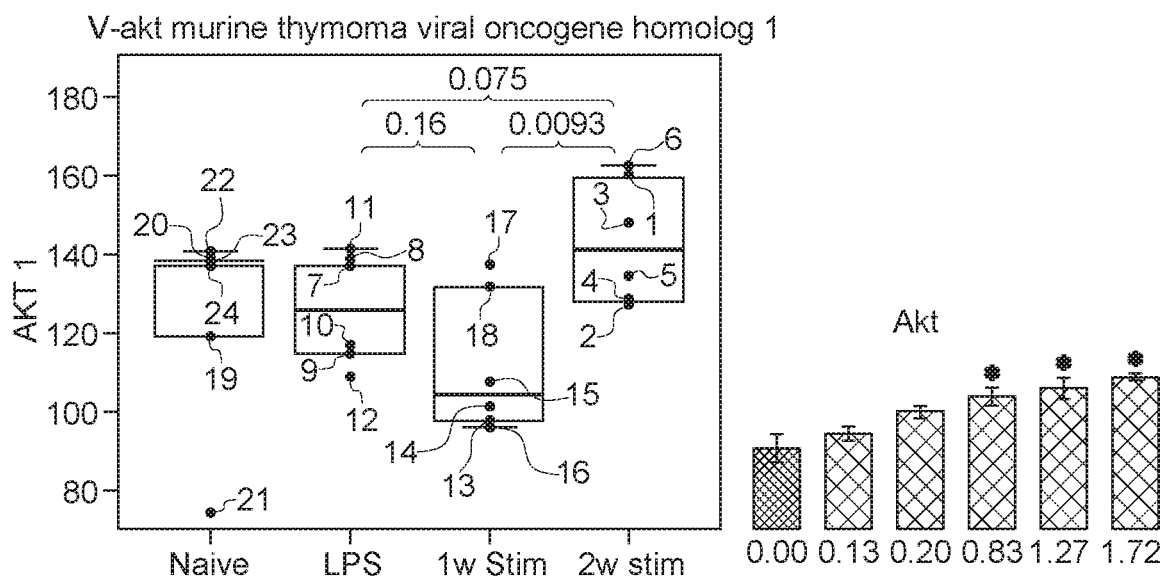
FIG. 10C shows the RNA and protein concentration of v-akt murine thymoma viral oncogene homolog 1 (Akt) in naïve spleens, sham control spleens, and ultrasound stimulated spleens according to embodiments of the disclosure.
Figure 10D:
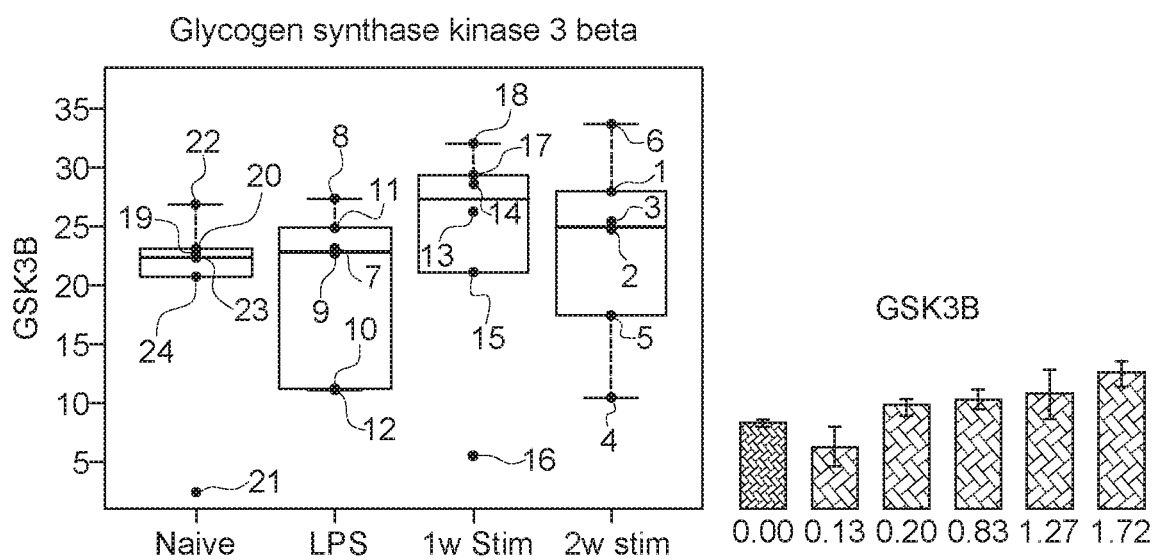
FIG. 10D shows the RNA and protein concentration of glycogen synthase kinase 3 beta (GSK3B) in naïve spleens, sham control spleens, and ultrasound stimulated spleens according to embodiments of the disclosure.
Figure 10E:
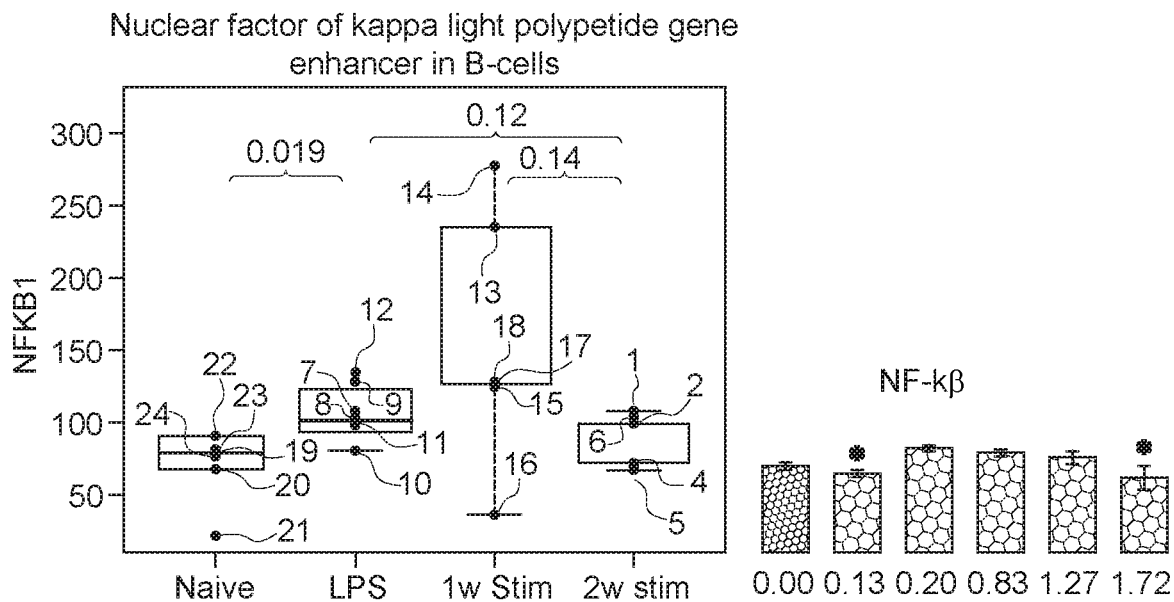
FIG. 10E shows the RNA and protein concentration of SRC proto-oncogene, non-receptor tyrosine kinase (c-Src) in naïve spleens, sham control spleens, and ultrasound stimulated spleens according to embodiments of the disclosure.
Figure 10F:
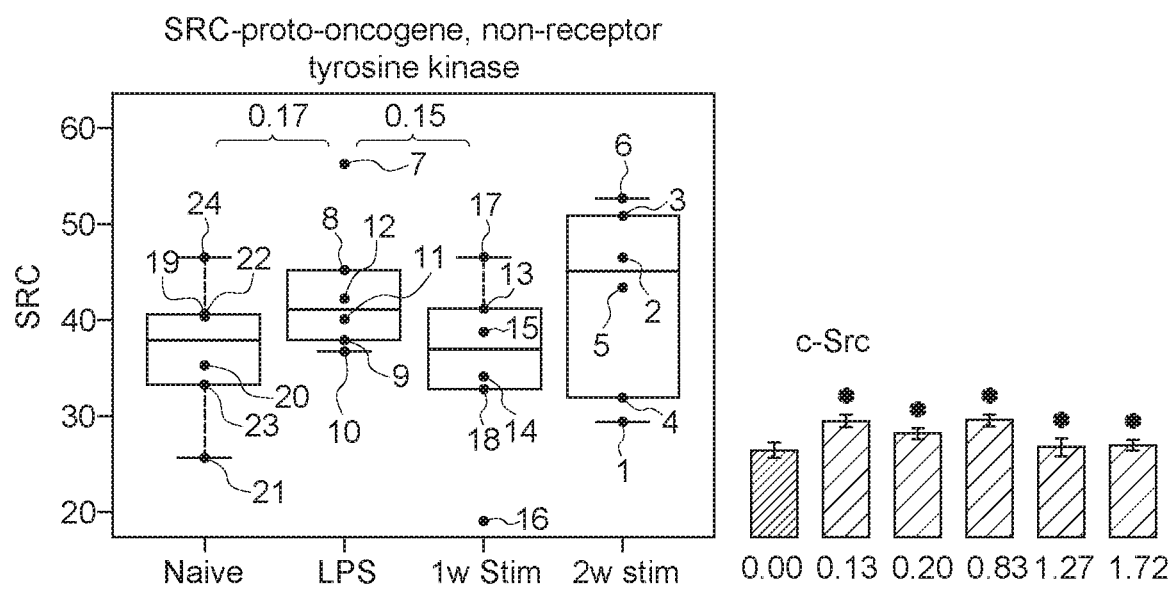
FIG. 10F shows the RNA and protein concentration of kappa light polypeptide gene enhancer in B-cells (NF-κβ) in naïve spleens, sham control spleens, and ultrasound stimulated spleens according to embodiments of the disclosure.
Figure 10G:
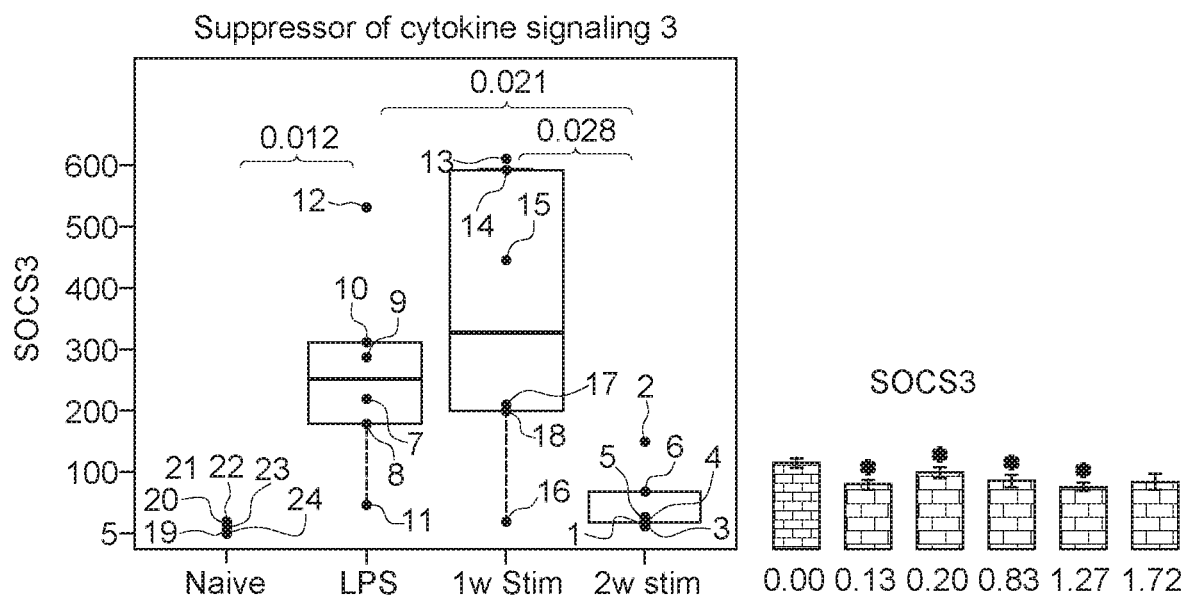
FIG. 10G shows the RNA and protein concentration of suppressor of cytokine signaling 3 (SOCS3) in naïve spleens, sham control spleens, and ultrasound stimulated spleens according to embodiments of the disclosure.

FIGS. 10A to 10G show the RNA concentrations of various genes in naïve rats, sham controls (i.e., rats that received LPS but not ultrasound stimulation), and rats that received LPS with ultrasound stimulation over a one week period and a two week period. FIGS. 10A to 10G also show the ultrasound activation level of various proteins at different ultrasound pressures. FIG. 10A shows the RNA concentration of mitogen-activated protein kinase 14 (p38) in naïve spleens, sham control spleens, and ultrasound stimulated spleens over a one week period and a two week period, and the ultrasound activation level of the corresponding gene protein p38 over increasing amounts of ultrasound pressure. FIG. 10B shows the RNA concentration of ribosomal protein S6 kinase B1 (p70S6K) in naïve spleens, sham control spleens, and ultrasound stimulated spleens over a one week period and a two week period, and the ultrasound activation level of the corresponding gene protein p70S6K over increasing amounts of ultrasound pressure. FIG. 10C shows the RNA concentration of v-akt murine thymoma viral oncogene homolog 1 (Akt) in naïve spleens, sham control spleens, and ultrasound stimulated spleens over a one week period and a two week period, and the ultrasound activation level of the corresponding gene protein Akt over increasing amounts of ultrasound pressure. FIG. 10D shows the RNA concentration of glycogen synthase kinase 3 beta (GSK3B) in naïve spleens, sham control spleens, and ultrasound stimulated spleens over a one week period and a two week period, and the ultrasound activation level of the corresponding gene protein GSK3B over increasing amounts of ultrasound pressure. FIG. 10E shows the RNA concentration of SRC proto-oncogene, non-receptor tyrosine kinase (c-Src) in naïve spleens, sham control spleens, and ultrasound stimulated spleens over a one week period and a two week period, and the ultrasound activation level of the corresponding gene protein c-Src over increasing amounts of ultrasound pressure. FIG. 10F shows the RNA concentration of nuclear factor of kappa light polypeptide gene enhancer in B-cells (NF-κβ) in naïve spleens, sham control spleens, and ultrasound stimulated spleens over a one week period and a two week period, and the ultrasound activation level of the corresponding gene protein NF-κβ over increasing amounts of ultrasound pressure. FIG. 10G shows the RNA concentration of suppressor of cytokine signaling 3 (SOCS3) in naïve spleens, sham control spleens, and ultrasound stimulated spleens over a one week period and a two week period, and the ultrasound activation level of the corresponding gene protein SOCS3 over increasing amounts of ultrasound pressure. As shown in FIGS. 10A to 10G, ultrasound activation levels (e.g., phosphorylation) of secondary messenger molecules are important to achieving a desired physiological outcome of ultrasound neuromodulation. However, RNA expression levels of the various proteins do not seem to change based on the treatment period (e.g., a one week period compared to a two week period).

Figure 11:
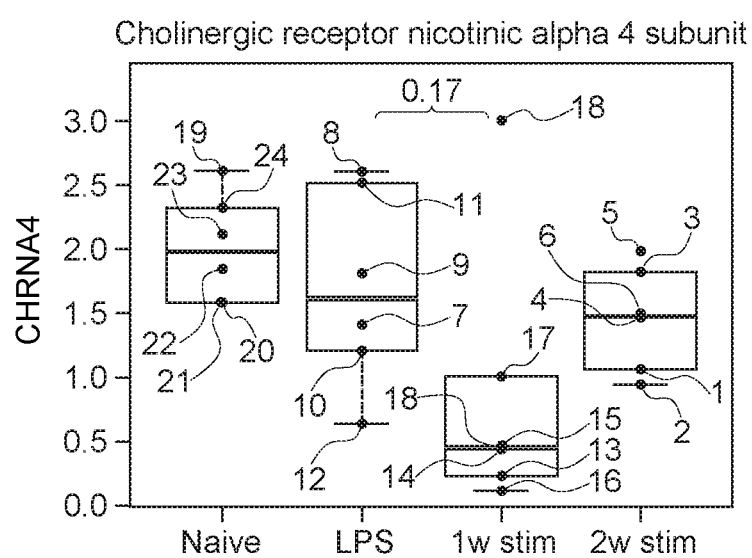
FIG. 11 shows the RNA concentration of cholinergic receptor nicotinic alpha 4 subunit (CHRNA4) in naïve spleens, sham control spleens, and ultrasound stimulated spleens according to embodiments of the disclosure.

FIG. 11 shows the RNA concentration of cholinergic receptor nicotinic alpha 4 subunit (CHRNA4) in naïve rats, sham controls, and rats that received LPS with ultrasound stimulation over a one week period and a two week period. As depicted in FIG. 11, the concentration of CHRNA4 in rats that received LPS with ultrasound stimulation over a one week period were found to be indicative of a reduced response of the cholinergic anti-inflammatory pathway (CAP) (e.g., to reduce systemic inflammation). However, the concentration of CHRNA4 in rats that received LPS with ultrasound stimulation over a two week period were found to correlate with the concentration of CHRNA4 found in the sham controls. Thus, ultrasound stimulation over a two week period was found to induce an increase in the expression of the CHRNA4 gene.

Figure 12A:
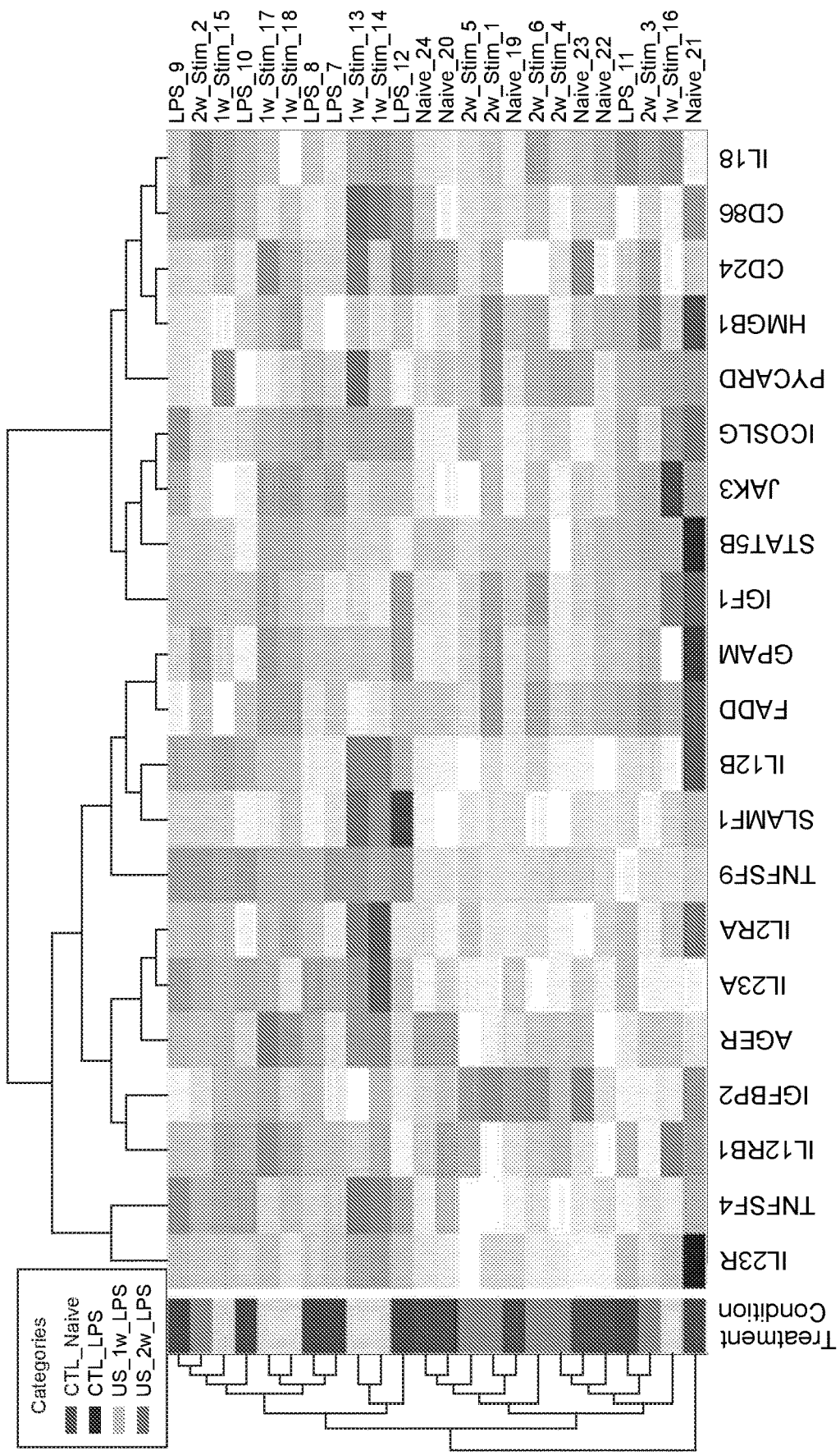
FIG. 12A shows transcriptome data of genes related to positive regulation of activated T cell proliferation (Gene Ontology: GO:0042104) according to embodiments of the disclosure.
Figure 12B:
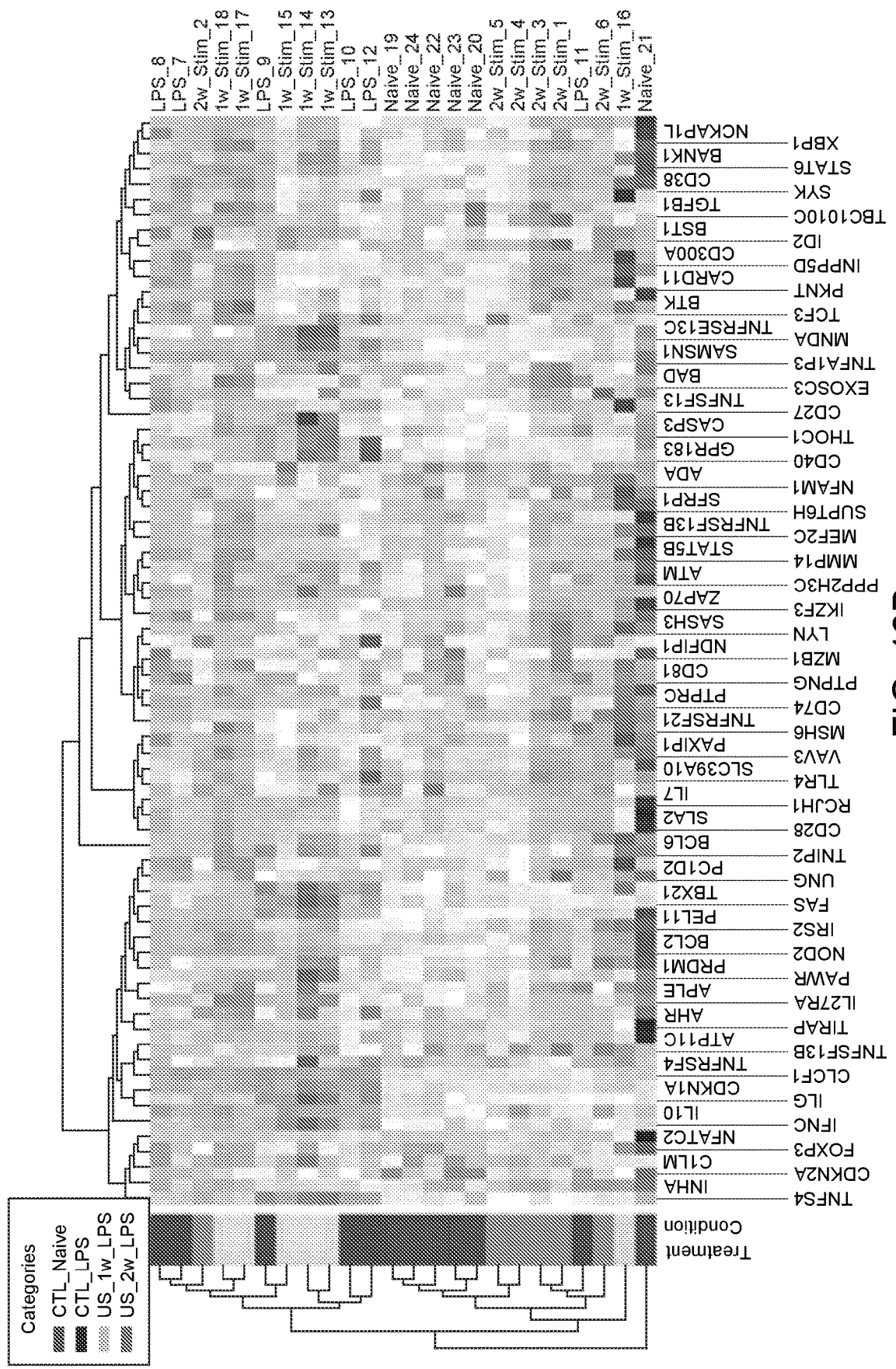
FIG. 12B shows transcriptome data of genes related to regulation of B cell activation (Gene Ontology: GO: 0050864) according to embodiments of the disclosure.

FIGS. 12A and 12B show transcriptome data of genes related to positive regulation of activated T cell proliferation (Gene Ontology: GO:0042104) and genes related to regulation of B cell activation (Gene Ontology: GO: 0050864) in naïve rats, sham controls, and rats that received LPS with ultrasound stimulation over a one week period and a two week period. As depicted in FIGS. 12A and 12B, ultrasound stimulation over a one week period was found to be insufficient to inhibit a proliferative response to LPS, but ultrasound stimulation over a two week period was found to be sufficient to inhibit a proliferative response to LPS.

Figure 13A:
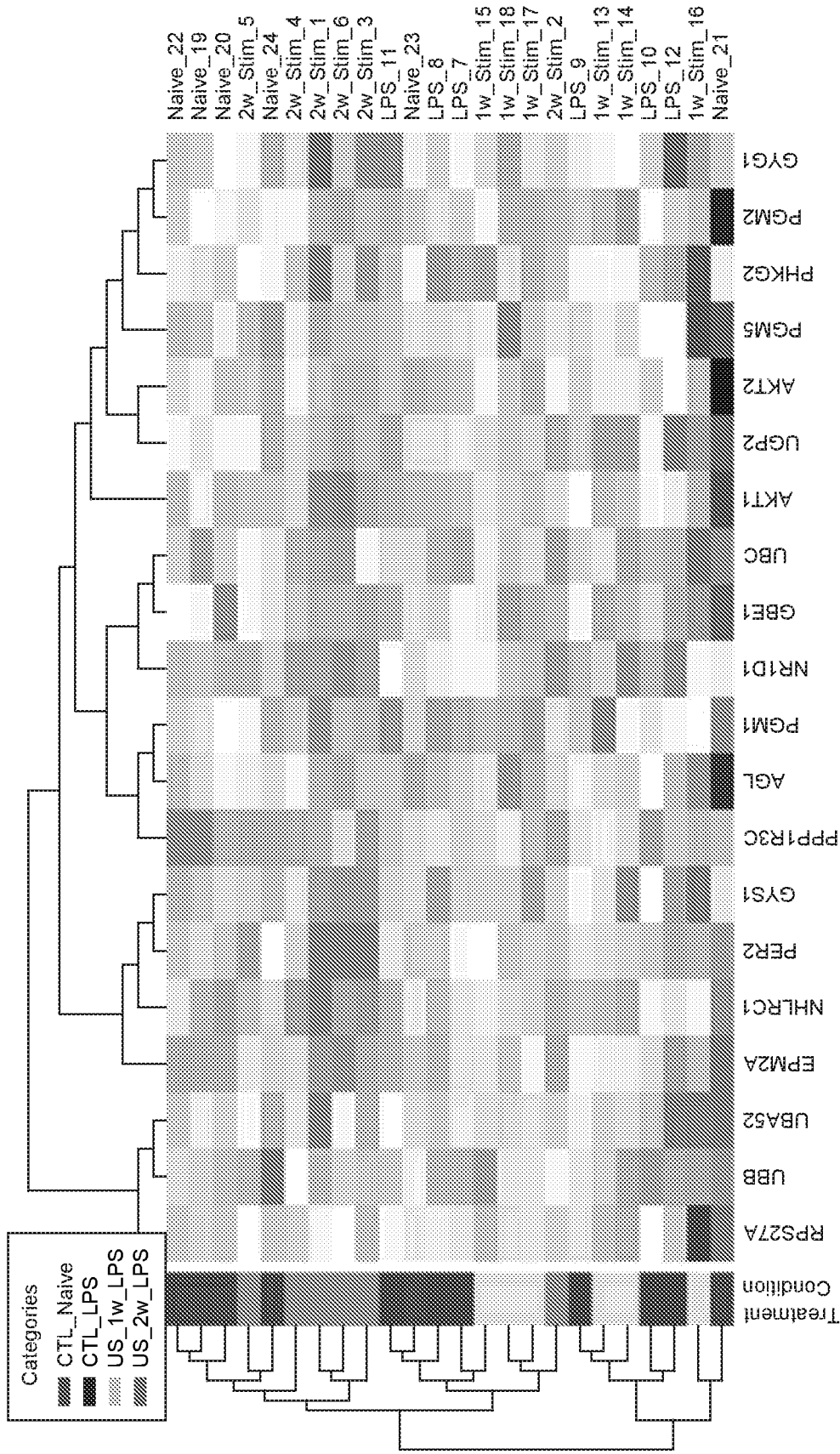
FIG. 13A shows transcriptome data of genes related to the glucan biosynthetic process (Gene Ontology: GO:0009250) according to embodiments of the disclosure.
Figure 13B:
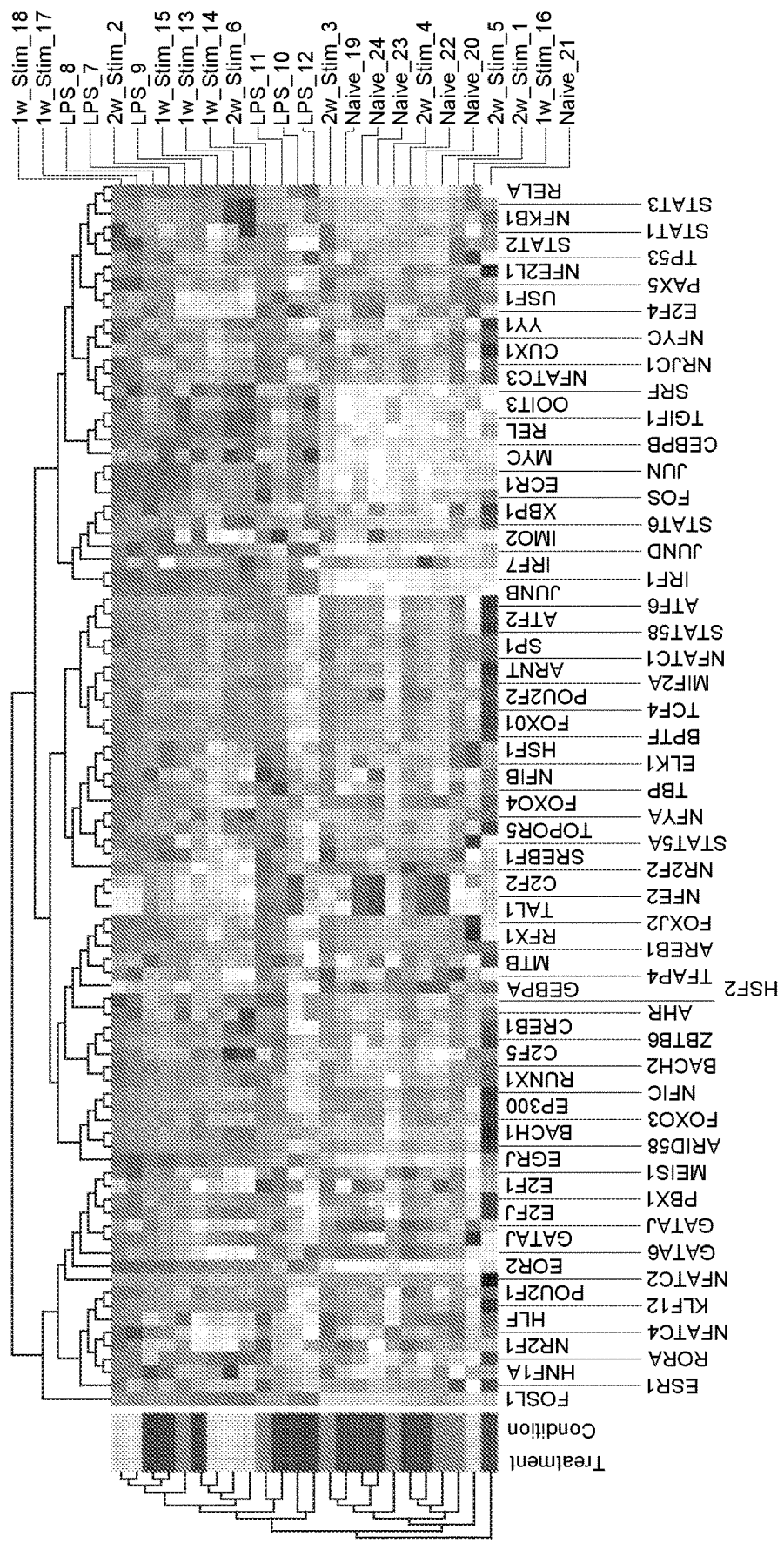
FIG. 13B shows transcriptome data of genes that encode proteins that are considered transcription factors according to embodiments of the disclosure.

FIGS. 13A and 13B show transcriptome data of genes related to the glucan biosynthetic process (e.g., the formation of glucans and polysaccharides consisting only of glucose residues (Gene Ontology: GO:0009250)) and genes that encode transcription factor proteins in naïve rats, sham controls, and rats that received LPS with ultrasound stimulation over a one week period and a two week period. As depicted in FIGS. 13A and 13B, ultrasound stimulation over a one week period was found to be insufficient to inhibit the response to LPS across multiple systems and/or molecular pathways, but ultrasound stimulation over a two week period was found to be sufficient to inhibit the response to LPS across multiple systems and/or molecular pathways.

Figure 14:
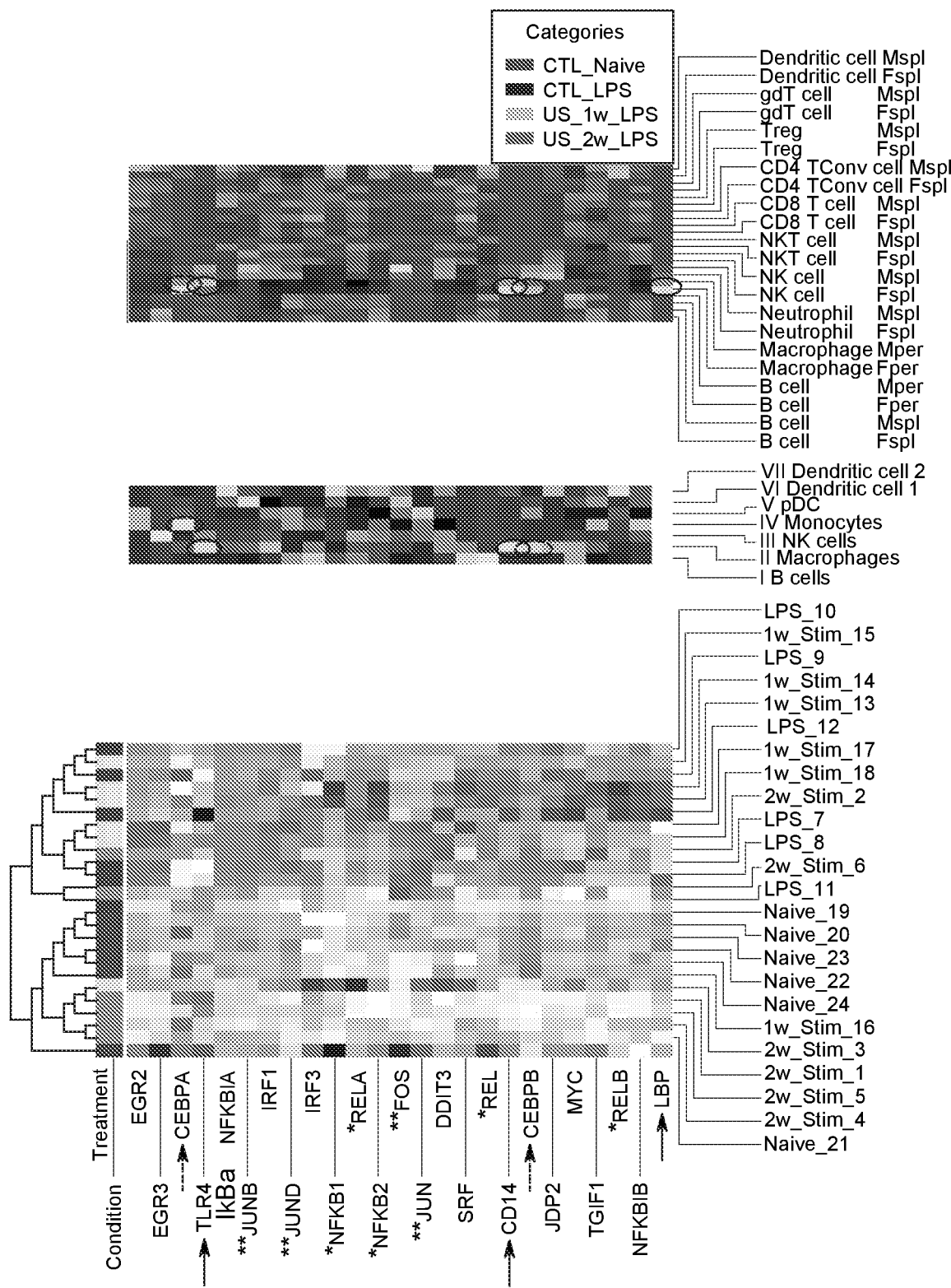
FIG. 14 shows transcriptome data of genes associated with the ability to detect LPS according to embodiments of the disclosure.

FIG. 14 shows transcriptome data of genes associated with the ability to detect LPS in naïve rats, sham controls, and rats that received LPS with ultrasound stimulation over a one week period and a two week period. As depicted in FIG. 14, ultrasound stimulation over a one week period was found to be insufficient to alter the expression of the genes (e.g., CEBPA, CEBPB, TLR4, CD14, and LBP) associated with the ability to detect LPS, but ultrasound stimulation over a two week period was found to be sufficient to alter the expression of the genes associated with the ability to detect LPS.

Figure 15:
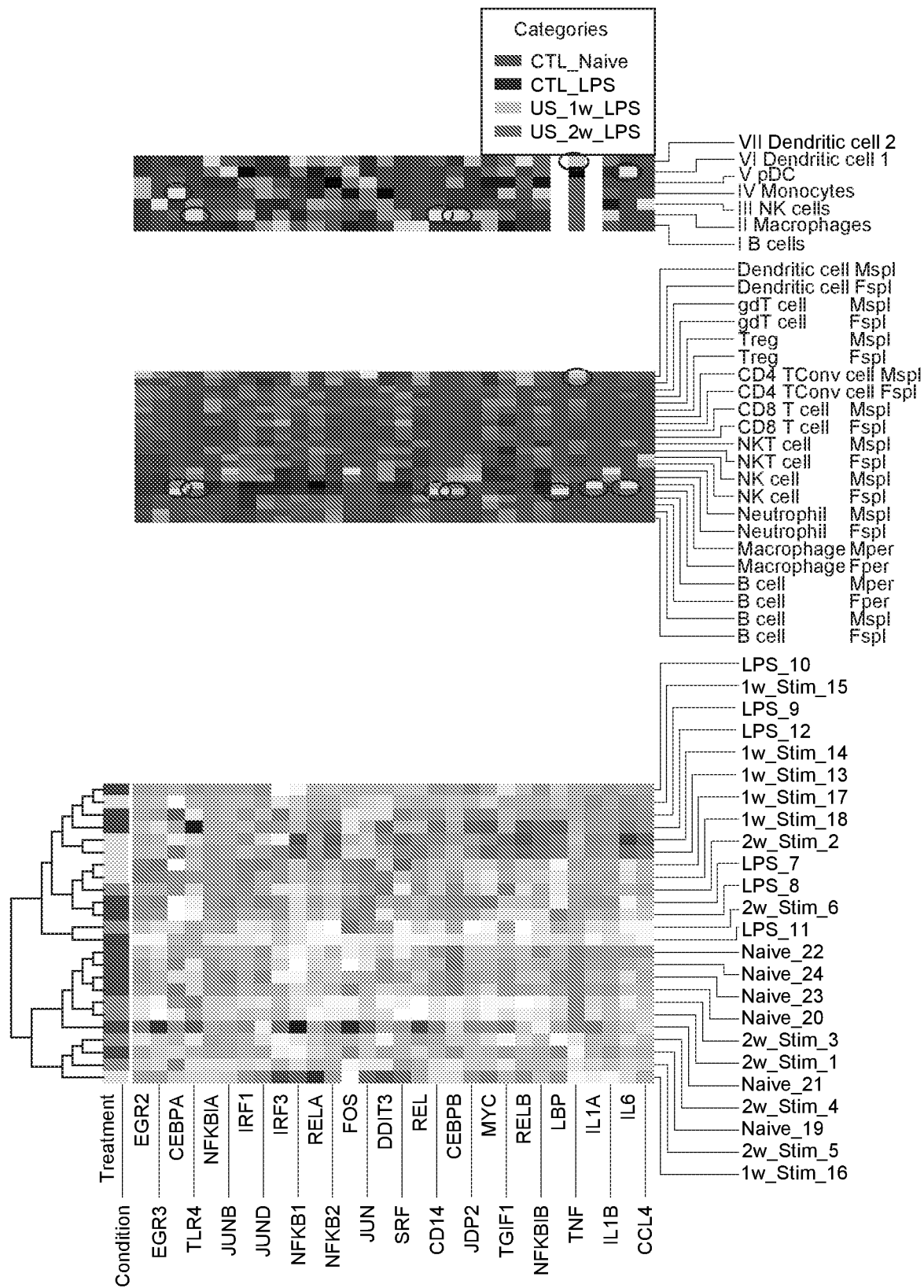
FIG. 15 shows transcriptome data of genes associated with the ability to detect LPS and the critical cytokine response genes according to embodiments of the disclosure.

FIG. 15 shows transcriptome data of genes associated with the innate immune system specifically the ability to detect and respond to LPS in naïve rats, sham controls, and rats that received LPS with ultrasound stimulation over a one week period and a two week period. As depicted in FIG. 15, ultrasound stimulation over a one week period was found to be insufficient to alter the expression of proinflammatory genes (e.g., TNF, IL-1A, IL-1B) associated with the innate immune system, but ultrasound stimulation over a two week period was found to be sufficient to alter the expression of the genes associated with innate immune system.

Figure 16A:
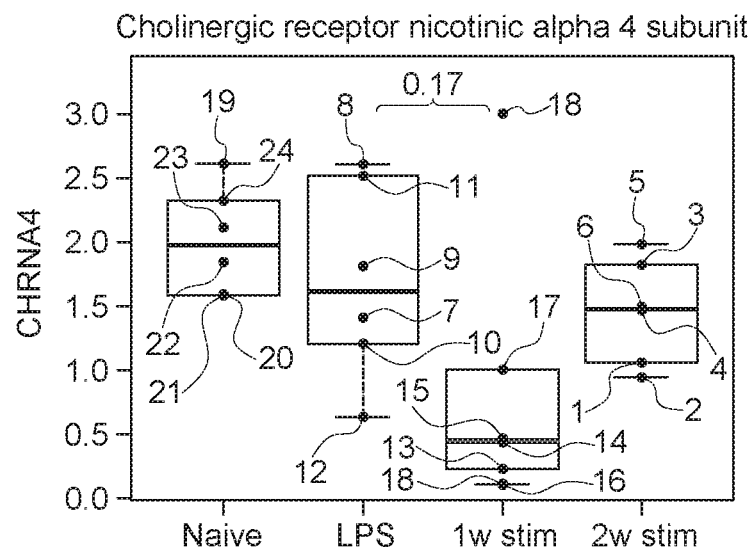
FIG. 16A shows the RNA concentration of cholinergic receptor nicotinic alpha 4 subunit (CHRNA4) in naïve spleens, sham control spleens, and ultrasound stimulated spleens according to embodiments of the disclosure.
Figure 16B:
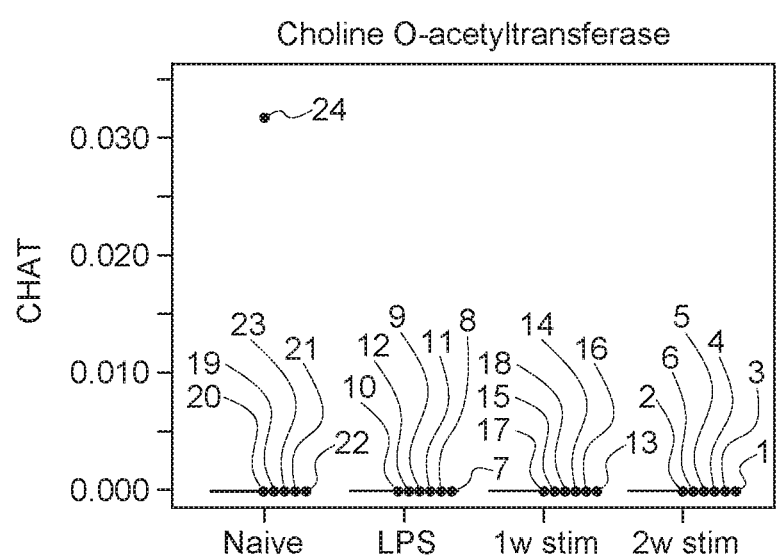
FIG. 16B shows the RNA concentration of choline O-acetyltransferase (CHAT) in naïve spleens, sham control spleens, and ultrasound stimulated spleens according to embodiments of the disclosure.
Figure 16C:
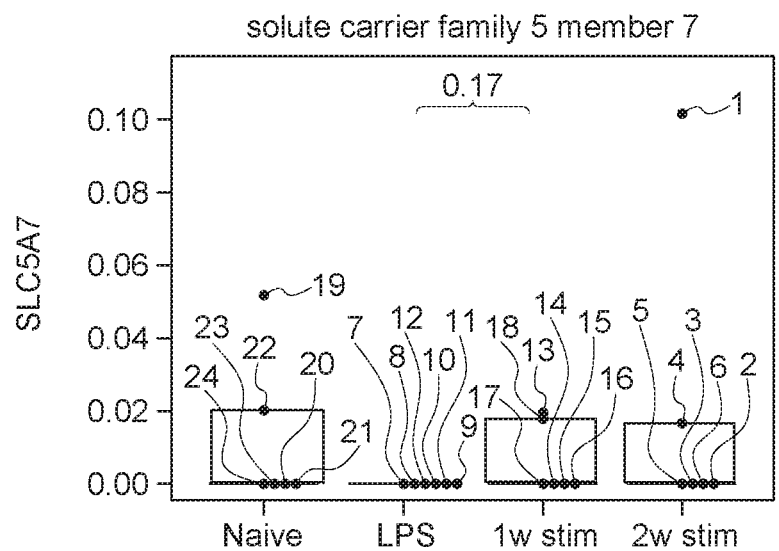
FIG. 16C shows the RNA concentration of solute carrier family 5 member 7 (SLC5A7) in naïve spleens, sham control spleens, and ultrasound stimulated spleens according to embodiments of the disclosure.
Figure 16D:
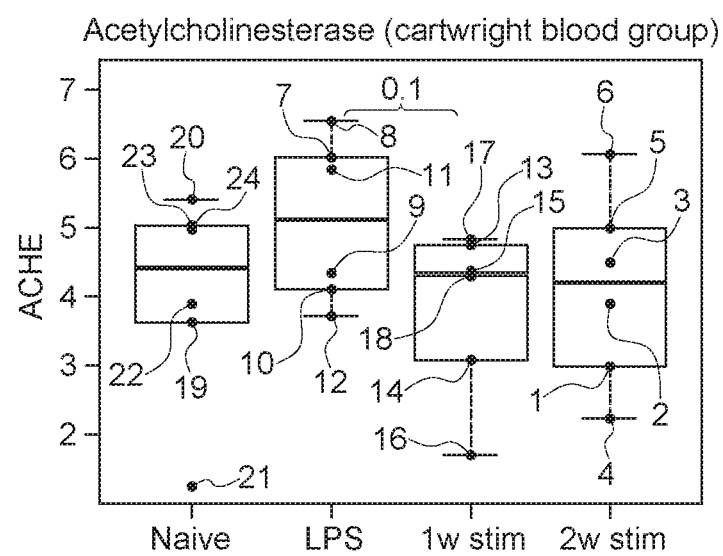
FIG. 16D shows the RNA concentration of acetylcholinesterase (Cartwright blood group) (ACHE) in naïve spleens, sham control spleens, and ultrasound stimulated spleens according to embodiments of the disclosure.
Figure 16E:
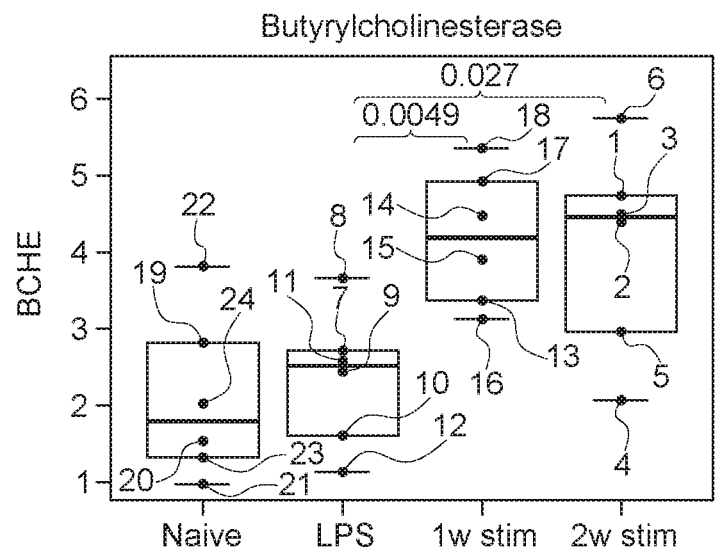
FIG. 16E shows the RNA concentration of butyrylcholinesterase (BCHE) in naïve spleens, sham control spleens, and ultrasound stimulated spleens according to embodiments of the disclosure.
Figure 16F:
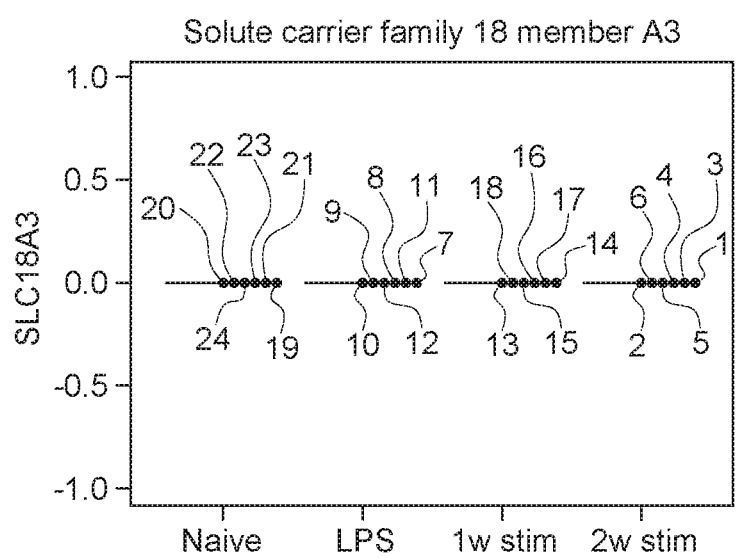
FIG. 16F shows the RNA concentration of solute carrier family 18 member A3 (SLC18A3) in naïve spleens, sham control spleens, and ultrasound stimulated spleens according to embodiments of the disclosure.

FIGS. 16A to 16G show the RNA concentrations of acetylcholine related genes in naïve rats, sham controls, and rats that received LPS with ultrasound stimulation over a one week period and a two week period. FIG. 16A shows the concentration of cholinergic receptor nicotinic alpha 4 subunit (CHRNA4) in naïve spleens, sham control spleens, and ultrasound stimulated spleens over a one week period and a two week period. FIG. 16B shows the concentration of choline O-acetyltransferase (CHAT) in naïve spleens, sham control spleens, and ultrasound stimulated spleens over a one week period and a two week period. FIG. 16C shows the concentration of solute carrier family 5 member 7 (SLC5A7) in naïve spleens, sham control spleens, and ultrasound stimulated spleens over a one week period and a two week period. FIG. 16D shows the concentration of acetylcholinesterase (Cartwright blood group) (ACHE) in naïve spleens, sham control spleens, and ultrasound stimulated spleens over a one week period and a two week period. FIG. 16E shows the concentration of butylrylcholinesterase (BCHE) in naïve spleens, sham control spleens, and ultrasound stimulated spleens over a one week period and a two week period. FIG. 16F shows the concentration of solute carrier family 18 member A3 (SLC18A3) in naïve spleens, sham control spleens, and ultrasound stimulated spleens over a one week period and a two week period. As depicted in FIG. 16A the expression level, CHRNA4, a subunit to an acetylcholine receptor, was found to initially decrease after one week of ultrasound stimulation but then surprisingly begin to increase after a two week period of ultrasound stimulation. Interestingly, the cholinesterase BCHE depicted in FIG. 16E hydrolyzes acetylcholine, and increases after one week of stimulation and remains elevated at two weeks. As such, nerve signaling such as the cholinergic anti-inflammatory pathway (CAP) that involve CHRNA4 and BCHE were found to be affected and modulated by ultrasound stimulation differently between a two week period of stimulation relative to a one week period of stimulation.

Figure 17A:
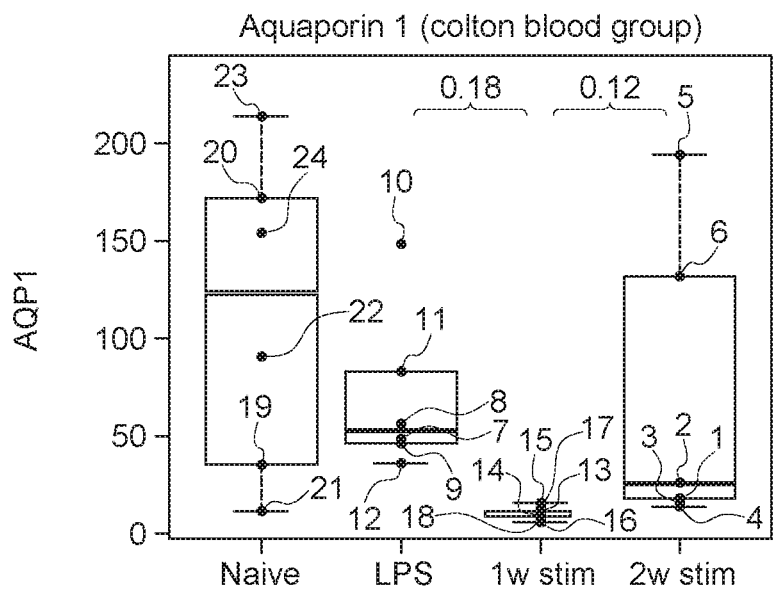
FIG. 17A shows the RNA concentration of aquaporin 1 (Colton blood group) in naïve spleens, sham control spleens, and ultrasound stimulated spleens according to embodiments of the disclosure.
Figure 17B:
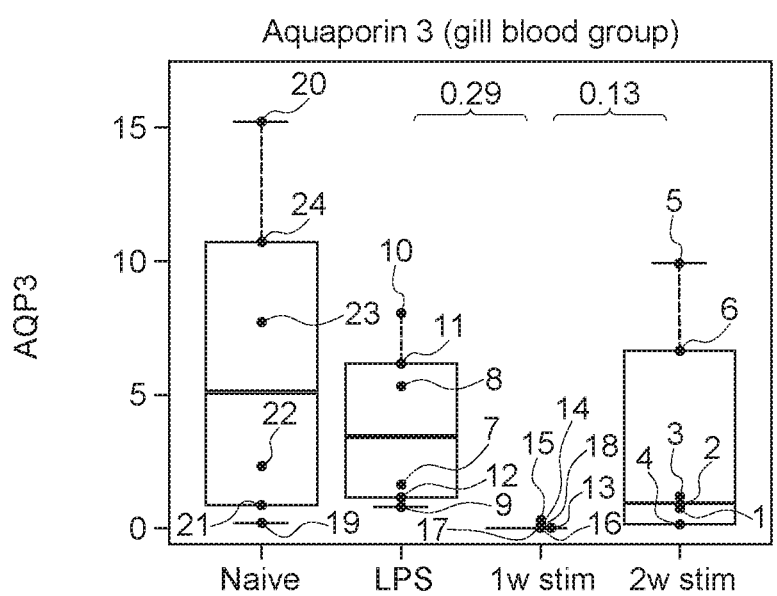
FIG. 17B shows the RNA concentration of aquaporin 3 (Gill blood group) in naïve spleens, sham control spleens, and ultrasound stimulated spleens according to embodiments of the disclosure.
Figure 18A:
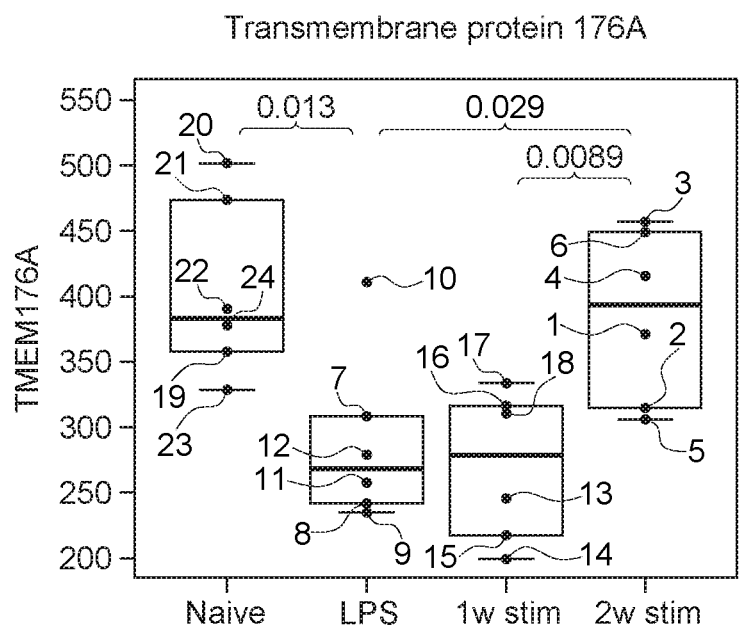
FIG. 18A shows the RNA concentration of transmembrane protein 176A (TMEM176A) in naïve spleens, sham control spleens, and ultrasound stimulated spleens according to embodiments of the disclosure.
Figure 18B:
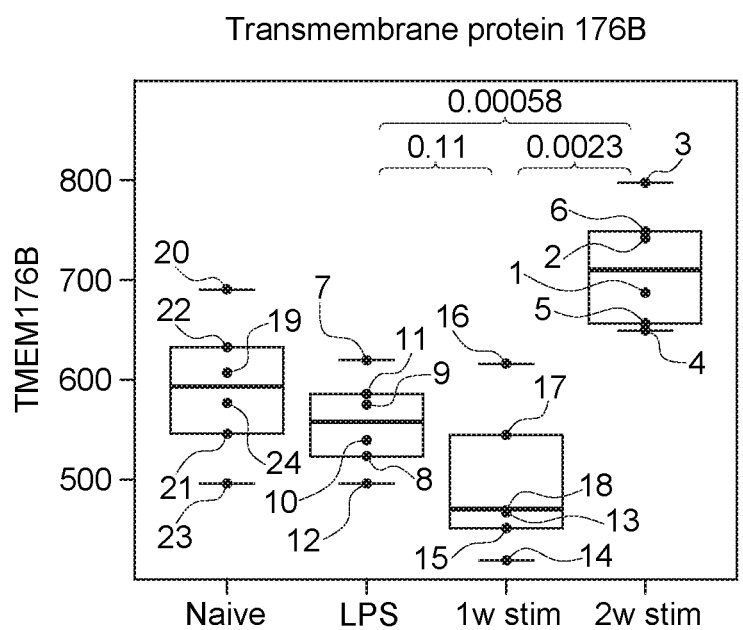
FIG. 18B shows the RNA concentration of transmembrane protein 176B (TMEM176B) in naïve spleens, sham control spleens, and ultrasound stimulated spleens according to embodiments of the disclosure.
Figure 18C:
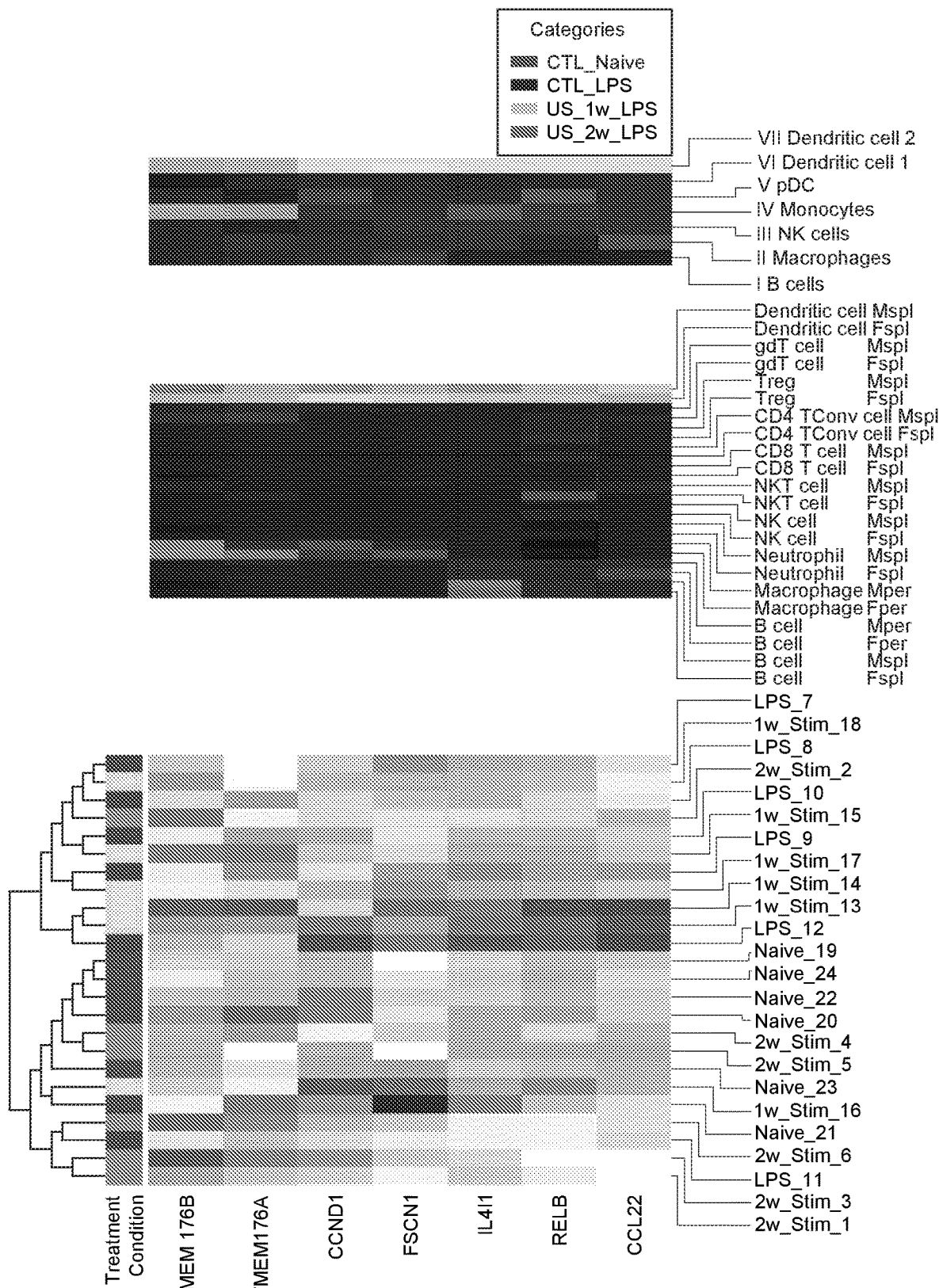
FIG. 18C shows transcriptome data of genes associated with TMEM176A and TMEM176B according to embodiments of the disclosure.

FIG. 17A shows the RNA concentration of aquaporin 1 (Colton blood group) in naïve rats, sham controls, and rats that received LPS with ultrasound stimulation over a one week period and a two week period. FIG. 17B shows the concentration of aquaporin 3 (Gill blood group) in naïve rats, sham controls, and rats that received LPS with ultrasound stimulation over a one week period and a two week period. FIG. 18A shows the concentration of transmembrane protein 176A (TMEM176A) in naïve rats, sham controls, and rats that received LPS with ultrasound stimulation over a one week period and a two week period. FIG. 18B shows the concentration of transmembrane protein 176B (TMEM176B) in naïve rats, sham controls, and rats that received LPS with ultrasound stimulation over a one week period and a two week period. TMEM176A and TMEM176B are associated with the immature state of dendritic cells. FIG. 18C shows transcriptome data of the genes associated with TMEM176A and TMEM176B in naïve rats, sham controls, and rats that received LPS with ultrasound stimulation over a one week period and a two week period grouped according to cluster analysis. As shown, the two-week group clustered together with the control/naïve group, while the one-week group clustered together with the control/sham group. Accordingly, cluster analysis (e.g. hierarchical, k means) may be used to identify gene expression profiles characteristic of a one-week response, a two-week response, a naïve response, and/or nonresponsiveness (similar to control/sham group) based on a closest match.

Figure 19:
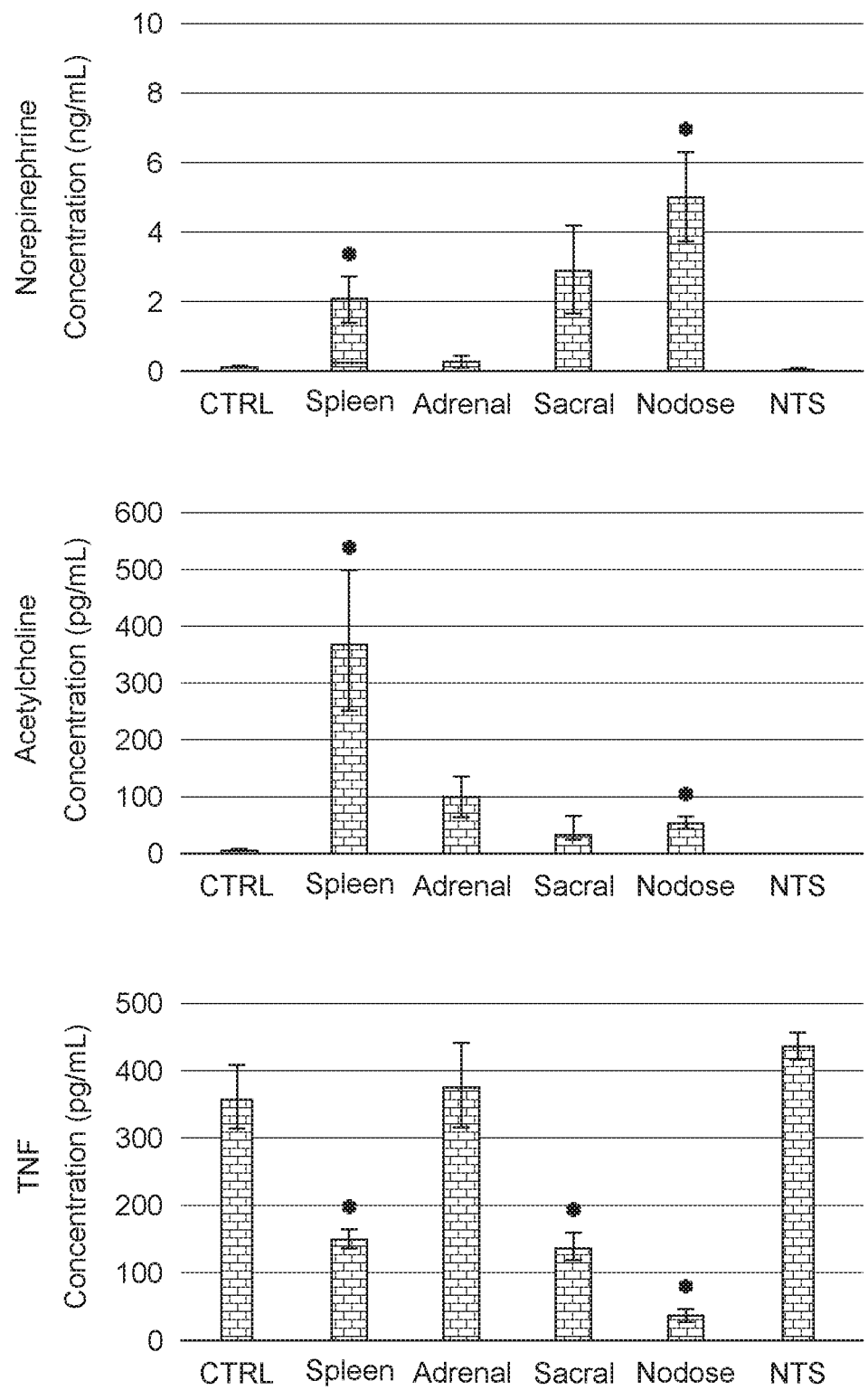
FIG. 19 shows the concentrations of norepinephrine, acetylcholine, and tumor necrosis factor in blood after ultrasound energy application to spleen, right adrenal gland, a sacral ganglion, a nodose ganglion, and nucleus tractus solitarii of lipopolysaccharides-induced hyperglycemia animal models according to embodiments of the disclosure.

FIG. 19 shows the average concentrations of circulating transient molecules (e.g., norepinephrine, acetylcholine, and tumor necrosis factor) relative to a control after ultrasound stimulation of spleen, right adrenal glands, sacral ganglia, nodose ganglia, or nucleus tractus solitarii. As shown in FIG. 19, an increase in concentration of norepinephrine as a result of ultrasound stimulation of the spleen produced an increase in the concentration of acetylcholine in the blood.

Modulating acetylcholine levels in the blood can affect multiple physiological processes. Intravenous injections of acetylcholine have been shown to decrease heart rate and cardiac output. Acetylcholine injections can cause vasodilation and decrease blood pressure through stimulation of muscarinic acetylcholine M3 receptors on endothelial cells and smooth muscle cells lining blood vessels. Within the gut, increased acetylcholine levels can stimulate intestinal motility and secretions. Endogenous acetylcholine is synthesized from choline by the choline o-acetyltransferase enzyme that is encoded by the CHAT gene. CHAT expression in the gastrointestinal tract is moderately high and is attributed to the high innervation by the vagus nerve. Within the spleen, the RNA expression of the CHAT gene was below the detection limit and effectively zero as illustrated in FIG. 17B. The source of acetylcholine in the blood plasma is mainly attributed to circulating mononuclear leukocytes (Fujii et al., *Expression and Function of the Cholinergic System in Immune Cells*, Frontiers in Immunology 8 (2017)). These circulating mononuclear leukocytes are in constant exchange with the spleen (Adams et al., *Exercise and Leukocyte Interchange Among Central Circulation, Lung, Spleen, and Muscle*, Brain, Behavior, and Immunity 25: 658-666 (2011)) and are consequentially exposed, trafficked, and modulated by short and long-term ultrasound spleen stimulation. For example, the secretion of the protein C-C motif chemokine ligand 4 (CCL4) in the spleen is used to traffic T cells (one type of mononuclear leukocyte) via the C-C chemokine receptor type 5 (CCR5) that is predominately expressed on T cells, macrophages, and dendritic cells. FIG. 9D demonstrates that there is a difference on the RNA expression of C-C motif chemokine ligand 4 (CCL4) between one and two weeks of ultrasound with a corresponding inferred change in trafficking and exchange between mononuclear leukocytes in the spleen and in circulation. Such modulation of trafficking would have a corresponding modulation in the concentration of acetylcholine in the blood plasma attributed to these circulating mononuclear leukocytes cells and the eventual downstream physiological changes from changes in plasma acetylcholine levels.

In another embodiment, the change in gene expression associated with a characteristic profile caused by neuromodulation may be used to change a patient's responsiveness to one or more other therapies. For example, the characteristic profile may be associated with an increase or decrease in expression of one or more cell surface receptors.

Technical effects of the invention include providing neuromodulation treatment to a subject over an extended period of time such that a desired acute response (e.g., the release of neurotransmitters or neuropeptides) to the neuromodulation treatment may be maintained while any undesired chronic effects of the neuromodulation treatment may be minimized. One or more treatment parameters of the neuromodulation treatment of a subject may be determined and/or modified based on any desired effects on the subject after a first series of energy application events. For example, a treatment period of energy application events, a treatment frequency of the energy application events within the treatment period, or a duration of a recovery period between subsequent neuromodulation treatment periods may be determined or modified based on assessed effects of the first series of energy application events of the neuromodulation treatment. In certain embodiments, the desired effect is a change in the expression level of certain genes in the subject. In certain embodiments, the desired effect is no change or minimal change to the expression level of certain genes in the subject. As such, the neuromodulation techniques provided herein may optimize the treatment parameters of neuromodulation treatment of a subject over an extended period of time such that a desired acute response to the neuromodulation treatment may be maintained while any undesired chronic effects of the neuromodulation treatment may be minimized.

One skilled in the art realizes the RNA sequencing could be performed to assess the RNA expression of all transcripts, transcripts of messenger RNA, or targeted RNA transcripts. Furthermore, RNA expression could be measured by RNA sequencing, by reverse transcription polymerase chain reaction (rt-PCR), and even by microarray technologies. Furthermore, RNA sequencing could be performed on single individual cells that were isolated from tissue samples with or without Fluorescence activated cell sorting.

RNA expression measures might be performed at multiple times and at distinct times defined by an individual's biological cycles and rhythms such as circadian rhythm. However, RNA expression measures may be limited and performed to confirm indirect measures that indicate changes in the tissue characteristics.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
   applying a first non-invasive ultrasound energy treatment to a region of interest of a subject according to a treatment protocol having a recovery period between subsequent ultrasound energy treatments to the subject to cause a change in concentration of one or more proteins at a distal site in the subject;
   measuring a concentration of the one or more proteins at the distal site and an expression level of one or more genes associated with the one or more proteins after applying the first non-invasive ultrasound energy treatment;
   adjusting a time of the recovery period before applying a second non-invasive ultrasound energy treatment to the region of interest based on a relationship between the concentration of the one or more proteins and the expression level of the one or more genes; and
   applying the second non-invasive ultrasound energy treatment after the adjusted time of the recovery period.

2. The method of claim 1, additionally comprising assessing a baseline expression level of the one or more genes before applying the first non-invasive ultrasound energy treatment, and wherein the expression level of the one or more genes is assessed relative to the baseline expression level of the one or more genes.

3. The method of claim 1, wherein measuring the expression level of the one or more genes comprises measuring the expression level of the one or more genes from RNA transcriptome data, mRNA transcriptome data, a cluster analysis of the RNA transcriptome data or the mRNA transcriptome data, or a combination thereof.

4. The method of claim 1, wherein the region of interest comprises a portion of a liver.

5. The method of claim 1, wherein the region of interest comprises a portion of a spleen.

6. The method of claim 1, wherein the region of interest comprises a portion of a pancreas.

7. The method of claim 1, wherein the relationship comprises an increase or decrease in the concentration of the one or more proteins at the distal site and a lack of change in the expression level of the one or more genes associated with the one or more proteins within a time window after applying the first non-invasive ultrasound energy treatment.

8. The method of claim 1, wherein the relationship comprises an increase or decrease in the concentration of the one or more proteins at the distal site and a change in the expression level of the one or more genes associated with the one or more proteins within a time window after applying the first non-invasive ultrasound energy treatment.

9. The method of claim 1, wherein the relationship is indicative of the expression level of the one or more genes changing from a baseline expression level before the first non-invasive ultrasound treatment, and wherein the time of the recovery period is set to an associated time of return of the expression level of the one or more genes to the baseline expression level.

10. The method of claim 1, comprising acquiring image data of an organ comprising the region of interest, wherein the region of interest is a subregion of the organ comprising at least one axon terminal and wherein the first noninvasive ultrasound energy treatment is applied only within the region of interest.

11. A method, comprising:
acquiring image data of an organ using an ultrasound probe to spatially select a region of interest of a subject, wherein the region of interest comprises only a subregion of the organ comprising one or more axon terminals;
applying, using the ultrasound probe, a non-invasive ultrasound energy treatment directly to the spatially selected region of interest according to a treatment protocol having one or more treatment parameters, to cause a targeted physiological outcome in the subject;
measuring a concentration of a neurotransmitter and an expression level of a gene associated with the neurotransmitter after applying the non-invasive ultrasound energy treatment; and
modifying the one or more treatment parameters associated with applying an additional non-invasive ultrasound energy treatment according to the treatment protocol based on a relationship between the expression level of the gene and the concentration of the neurotransmitter associated with the gene;
wherein the gene encodes for a cell receptor of the neurotransmitter, wherein the relationship is a decrease in the expression level of the gene, and wherein modifying the one or more treatment parameters comprises extending a recovery time before applying the additional non-invasive ultrasound treatment until the decrease is no longer observed.

12. The method of claim 11, wherein applying the non-invasive ultrasound energy treatment causes the targeted physiological outcome at a distal site in the subject without inducing a change to the expression level of the gene in the region of interest.

13. The method of claim 11, wherein the targeted physiological outcome comprises a change in concentration of an enzyme responsible for synthesis or secretion of circulating vasorelaxant molecules, circulating vasoconstricting molecules, or both, and wherein the gene encodes the enzyme.

14. The method of claim 13, wherein the targeted physiological outcome comprises a change in blood pressure and the circulating vasorelaxant molecules comprises acetylcholine.

15. A method, comprising:
applying a first non-invasive ultrasound energy treatment to a region of interest of a subject according to a treatment protocol having one or more treatment parameters, to cause a change in concentration of one or more proteins at a distal site in the subject, wherein the one or more treatment parameters comprise a recovery period of time between sequential ultrasound energy treatments to the subject, and wherein an ultrasound energy of the first non-invasive ultrasound energy treatment is focused within the region of interest, the region of interest comprising an organ subregion having a volume of less than 25 cubic millimeters (mm$^3$);
measuring a concentration of the one or more proteins at the distal site and RNA transcription of a gene associated with the one or more proteins in the region of interest after applying the first non-invasive ultrasound energy treatment; and
modifying the recovery period of time before applying a second non-invasive ultrasound energy treatment based on a relationship between the RNA transcription of the gene and the concentration of the one or more proteins associated with the gene.

16. The method of claim 15, wherein measuring the RNA transcription of the gene comprises sequencing RNA from blood cells extracted from the region of interest.

* * * * *